US012590110B2

(12) United States Patent
Blumstock et al.

(10) Patent No.: US 12,590,110 B2
(45) Date of Patent: Mar. 31, 2026

(54) AMORPHOUS (A-POLYMORPHIC) PSILOCYBIN

(71) Applicant: Diamond Therapeutics Inc., Toronto (CA)

(72) Inventors: Judith Blumstock, Toronto (CA); David Roger Brown, Pickering (CA); Christian Steup, Kelkheim (DE); Marc Zeplichal, Reinheim (DE)

(73) Assignee: Diamond Therapeutics Inc., Toronto (CA)

( * ) Notice: Subject to any disclaimer, the term of this patent is extended or adjusted under 35 U.S.C. 154(b) by 0 days.

(21) Appl. No.: 18/764,635

(22) Filed: Jul. 5, 2024

(65) Prior Publication Data

US 2024/0360161 A1 Oct. 31, 2024

Related U.S. Application Data

(63) Continuation of application No. PCT/IB2023/000349, filed on Jun. 8, 2023.

(60) Provisional application No. 63/350,828, filed on Jun. 9, 2022.

(51) Int. Cl.

| | |
|---|---|
| ***C07F 9/572*** | (2006.01) |
| ***A61K 9/14*** | (2006.01) |
| ***A61K 9/19*** | (2006.01) |
| ***A61K 31/4045*** | (2006.01) |
| ***A61K 31/675*** | (2006.01) |

(52) U.S. Cl.

CPC ............ *C07F 9/5728* (2013.01); *A61K 9/145* (2013.01); *A61K 9/146* (2013.01); *A61K 9/19* (2013.01); *A61K 31/4045* (2013.01); *A61K 31/675* (2013.01)

(58) Field of Classification Search

CPC ......... C07F 9/5728; A61K 9/145; A61K 9/19; A61K 31/675

See application file for complete search history.

(56) References Cited

U.S. PATENT DOCUMENTS

| | | | |
|---|---|---|---|
| 3,183,172 | A | 5/1965 | Roger et al. |
| 3,192,111 | A | 6/1965 | Albert et al. |
| 7,229,784 | B2 | 6/2007 | Holtzman et al. |
| 10,064,856 | B2 | 9/2018 | Bosse et al. |
| 10,519,175 | B2 | 12/2019 | Londesbrough et al. |
| 10,596,378 | B2 | 3/2020 | Rustick |
| 10,729,706 | B2 | 8/2020 | Kucuksen et al. |
| 10,738,268 | B2 | 8/2020 | Leo |
| 10,947,257 | B2 | 3/2021 | Londesbrough et al. |
| 10,954,259 | B1 | 3/2021 | Londesbrough et al. |
| 11,766,445 | B2 | 9/2023 | LaRosa et al. |
| 2012/0108510 | A1 | 5/2012 | Young et al. |
| 2012/0159656 | A1 | 6/2012 | Gerber et al. |
| 2014/0052474 | A1 | 2/2014 | Madan et al. |
| 2014/0114904 | A1 | 4/2014 | Choo et al. |
| 2016/0138111 | A1 | 5/2016 | Knudsen |
| 2016/0270656 | A1 | 9/2016 | Samec et al. |
| 2017/0039344 | A1 | 2/2017 | Bitran et al. |
| 2017/0216219 | A1 | 8/2017 | Dhar et al. |
| 2017/0283884 | A1 | 10/2017 | Knudsen |
| 2018/0021326 | A1 | 1/2018 | Stamets |
| 2018/0032698 | A1 | 2/2018 | Lau et al. |
| 2018/0221396 | A1 | 8/2018 | Chadeayne |
| 2019/0105313 | A1 | 4/2019 | Stamets |
| 2019/0142851 | A1 | 5/2019 | Chadeayne |
| 2019/0192498 | A1 | 6/2019 | Stamets |
| 2019/0350949 | A1 | 11/2019 | Kucuksen et al. |
| 2020/0085816 | A1 | 3/2020 | Raz |
| 2020/0147038 | A1 | 5/2020 | Russ et al. |
| 2020/0199161 | A1 | 6/2020 | Londesbrough et al. |
| 2020/0215297 | A1 | 7/2020 | Rabin et al. |
| 2020/0331939 | A1 | 10/2020 | Londesbrough et al. |
| 2021/0033618 | A1 | 2/2021 | Innocenzi et al. |
| 2021/0236523 | A1 | 8/2021 | Schindler et al. |
| 2022/0096504 | A1 | 3/2022 | Blumstock et al. |
| 2023/0113351 | A1 | 4/2023 | Blumstock et al. |
| 2023/0233584 | A1 | 7/2023 | Blumstock et al. |
| 2023/0248705 | A1 | 8/2023 | Gobbi et al. |
| 2024/0120053 | A1 | 4/2024 | Blumstock et al. |
| 2025/0171472 | A1 | 5/2025 | Blumstock et al. |
| 2025/0176904 | A1 | 6/2025 | Blumstock et al. |
| 2025/0182901 | A1 | 6/2025 | Tyler et al. |

FOREIGN PATENT DOCUMENTS

| | | | | |
|---|---|---|---|---|
| CA | 3133547 | * | 10/2021 | ......... A61K 31/4045 |
| CN | 108619214 | A | 10/2018 | |
| EP | 3675137 | A1 | 7/2020 | |
| JP | 2007525405 | A | 9/2007 | |
| WO | WO-2014140925 | A2 | 9/2014 | |
| WO | WO-2016138138 | A1 | 9/2016 | |

(Continued)

OTHER PUBLICATIONS

Sherwood, Synthesis, 2020, 52, 688-694 (Year: 2020).*

Palfreyman (Journal of Psychopharmacology, 39(12), 2025) (Year: 2025).*

Anderson, Thomas, et al. Psychedelic microdosing benefits and challenges: an empirical codebook. Harm Reduction Journal 16(1):1-10 (2019).

EP21848825.2 Partial Supplemental European Search Report dated Aug. 14, 2024.

Horsley, Rachel R., et al. Psilocin and ketamine microdosing: effects of subchronic intermittent microdoses in the elevated plus-maze in male Wistar rats. Behavioural Pharmacology 29(6):530-536 (2018).

Lea, Toby, et al. Microdosing psychedelics: Motivations, subjective effects and harm reduction. International Journal of Drug Policy 75:1-9 (2019).

(Continued)

*Primary Examiner* — Susanna Moore
*Assistant Examiner* — Luisalberto Gonzalez
(74) *Attorney, Agent, or Firm* — WILSON SONSINI GOODRICH & ROSATI

(57) ABSTRACT

Disclosed herein are compositions comprising amorphous psilocybin. The amorphous psilocybin may be a synthetic, a-polymorphic psilocybin. Also disclosed herein are methods of treatment using amorphous psilocybin and methods of manufacturing amorphous psilocybin.

18 Claims, 3 Drawing Sheets

(56) References Cited

FOREIGN PATENT DOCUMENTS

| | | | | |
|---|---|---|---|---|
| WO | WO-2018067571 A2 | 4/2018 | | |
| WO | WO-2018135943 A1 | 7/2018 | | |
| WO | WO-2018148605 A1 | 8/2018 | | |
| WO | WO-2018195455 A1 | 10/2018 | | |
| WO | WO-2019079742 A1 | 4/2019 | | |
| WO | WO-2019161050 A1 | 8/2019 | | |
| WO | WO-2019180309 A1 | 9/2019 | | |
| WO | WO-2019246532 A1 | 12/2019 | | |
| WO | WO-2020041329 A1 | 2/2020 | | |
| WO | WO-2020157569 A1 | 8/2020 | | |
| WO | WO-2020181194 A1 | 9/2020 | | |
| WO | WO-2020212951 A1 | 10/2020 | | |
| WO | WO-2021003467 A1 | 1/2021 | | |
| WO | WO-2021019023 A1 | 2/2021 | | |
| WO | WO-2021030571 A1 | 2/2021 | | |
| WO | WO-2021059202 A1 | 4/2021 | | |
| WO | WO-2021072530 A1 | 4/2021 | | |
| WO | WO-2021108911 A1 | 6/2021 | | |
| WO | WO-2022016289 A1 * | 1/2022 | ........... | C07D 209/12 |
| WO | WO-2022023812 A1 | 2/2022 | | |
| WO | WO-2022023813 A1 | 2/2022 | | |
| WO | WO-2022189855 A1 | 9/2022 | | |
| WO | WO-2022243285 A1 * | 11/2022 | ........... | A61K 9/0056 |
| WO | WO-2023078604 A1 | 5/2023 | | |
| WO | WO-2023170441 A1 | 9/2023 | | |
| WO | WO-2023227941 A1 | 11/2023 | | |
| WO | WO-2023237930 A1 * | 12/2023 | ........... | A61K 31/675 |
| ZA | 200002311 B | 11/2001 | | |

OTHER PUBLICATIONS

Ansel, Howard C. et al. Pharmaceutical Dosage Forms and Drug Delivery System, Seventh Edition. Lippincott Wiliams (1999).
Anwer, Md. K., et al. Preparation, Evaluation and Bioavailability Studies of Eudragit Coated PLGA Nanoparticles for Sustained Release of Eluxadoline for the Treatment of Irritable Bowel Syndrome. Frontiers in Pharmacology 8(844):1-11 (2017).
Bundgaard, Hans. Design of Prodrugs. Elsevier 7(9):1-31 (1985).
Co-pending U.S. Appl. No. 18/840,679, inventors William; James Tyler et al., filed Aug. 22, 2024.
Co-pending U.S. Appl. No. 18/841,530, inventors Blumstock; Judith et al., filed Aug. 26, 2024.
Gennaro, Alfonso R. et al. Remington's Pharmaceutical Sciences, latest edition. Mack Publishing Co, Easton PA (1991).
Gennaro, Alfonso R. Remington: Practice of The Science and Pharmacy, 19th Edition. Mack Publishing Company (1995).
Hoover, John E. et al. Remington's Pharmaceutical Sciences. Mack Publishing Company 1-5 (1975).
Jacques, Jean et al. Enantiomers, Racemates and Resolutions. John Wiley and Sons (1981).
Lieberman, Herbert A, and Leon Lachman. Pharmaceutical Dosage Forms: Tablets. Marcel Decker (1980).
PCT/IB2023/000292 International Search Report and Written Opinion dated Oct. 17, 2023.
Stahl, P Heinrich, and Camille G. Wermuth. Handbook of Pharmaceutical Salts: Properties, Selection, and Use. Verlag Helvetica Chimica Acta and Wiley-VCH (2002).
Stevanovic, D. Quality of Life Enjoyment and Satisfaction Questionnaire-Short Form for Quality of Life Assessments in Clinical Practice: A Psychometric Study. Journal of Psychiatric and Mental Health Nursing 18(8):744-750 (2011).
U.S. Appl. No. 18/814,163 Office Action dated Oct. 11, 2024.
30 Day Microdosing Experiment. Thestonedyogagirl, Reddit, Aug. 22, 2019; [retrieved on Jul. 22, 2024]. Available at URL:https://www.reddit.com/r/microdosing/comments/ctkz2k/30_day_microdosing_experiment pp. 1-2.
Aghajanian et al.: Serotonin and Hallucinogens. Neuropsychopharmacology. 21(2 Suppl): 16S-23S (1999).
Akbari et al.: Development and evaluation of buccoadhesive propranolol hydrochloride tablet formulations: effect of fillers. Farmaco 59(2):155-161 (2004).
Andersson et al.: Psychoactive substances as a last resort-a qualitative study of self-treatment of migraine and cluster headaches. Harm Reduct J. 2017 14(1):60, pp. 1-10 doi:10.1186/s12954-017-0186-6 (2017).
Anxiety Disorders. Mayo Clinic, Nov. 14, 2018; [retrieved on Jul. 22, 2024]. Available at URL:https://web.archive.org/web/20181114083639/https:/www.mayoclinic.org/diseases-conditions/anxiety/symptoms-causes/syc-20350961 pp. 1-5.
Aronson: Plant Poisons and Traditional Medicines. Manson's Tropical Infectious Diseases (Twenty-Third Edition),pp. 1128-115010.e6 doi:10.1016/B978-0-7020-5101-2.00077-7 (2014).
Artusi et al.: Buccal delivery of thiocolchicoside: in vitro and in vivo permeation studies. Int J Pharm. 250(1):203-213 (2003).
Berge, Stephen M. et al. Pharmaceutical Salts. Journal of Pharmaceutical Sciences 66(1):1-19 (1977).
Bershad et al.: Preliminary Report on the Effects of a Low Dose of LSD on Resting-State Amygdala Functional Connectivity. Biol Psychiatry Cogn Neurosci Neuroimaging 5(4):461-467 doi:10.1016/j.bpsc.2019.12.007 (2020).
Bogenschutz et al.: Psilocybin-assisted treatment for alcohol dependence: a proof-of-concept study. J Psychopharmacol 29(3):289-299 doi:10.1177/0269881114565144 (2015).
Boyd, medically reviewed by Miller: Lack of motivation: common causes, related health conditions, and more. pp. 1-4. URL:https://www.everlywell.com/blog/testosterone/lack-of-motivation-common-causes/ [retrieved online Mar. 15, 2023] (2019).
Buchborn et al.: Repeated lysergic acid diethylamide in an animal model of depression: Normalisation of learning behaviour and hippocampal serotonin 5-HT2 signalling. J Psychopharmacol. 28(6):545-552 doi:10.1177/0269881114531666 (2014).
Bundgaard et al. Chapter 5: Design and Application of Prodrugs. Textbook of Drug Design and Development. 113-191 (1991).
Bundgaard, Hans., Means to Enhance Penetration: Prodrugs as a Means to Improve the Delivery of Peptide Drugs. Advanced Drug Delivery Review 8:1-38 (1992).
Cameron et al.: Chronic, Intermittent Microdoses of the Psychedelic N, N-Dimethyltryptamine (DMT) Produce Positive Effects on Mood and Anxiety in Rodents. CS Chem Neurosci. 10(7):3261-3270 doi:10.1021/acschemneuro.8b00692 (2019).
Carhart-Harris et al.: Neural correlates of the psychedelic state as determined by fMRI studies with psilocybin. Proc Natl Acad Sci USA 109(6):2138-2143 doi:10.1073/pnas.1119598109 (2012).
Carhart-Harris et al.: Psilocybin with psychological support for treatment-resistant depression: an open-label feasibility study. Lancet Psychiatry 3: 619-627 (2016).
Carhart-Harris et al.: Psilocybin with psychological support for treatment-resistant depression: six-month follow-up. Psychopharmacology (Berl). 235(2):399-408 (2018).
Cavanna et al.: Microevidence for microdosing with psilocybin mushrooms: a double-blind placebo-controlled study of subjective effects, behavior, creativity, perception, cognition, and brain activity. bioRxiv pre-print, pp. 1-36 doi:10.1101/2021.11.30.470657 (2021).
Collett, John H, et al., Dosage Regimens. Aultons Pharmaceutics :7 Pages (2016).
Daniel et al.: Clinical potential of psilocybin as a treatment for mental health conditions. Ment Health Clin [Internet]. 7(1): 24-28 (2017).
De Gregorio et al.: Hallucinogens in Mental Health: Preclinical and Clinical Studies on LSD, Psilocybin, MDMA, and Ketamine. J Neurosci. 41(5):891-900 doi:10.1523/JNEUROSCI.1659-20.2020 (2021).
De Gregorio et al.: Lysergic acid diethylamide (LSD) promotes social behavior through mTORC1 in the excitatory neurotransmission. PNAS USAS 118(5):e2020705118 doi:10.1073/pnas.2020705118 [1-9] (2021).
Desert Hope Treatment Center, Oral drug use: Signs, effects, & types. Retrieved from the Internet on Dec. 19, 2023.
Dolder et al.: Pharmacokinetics and Concentration-Effect Relationship of Oral LSD in Humans. Int J. Neuropsychopharmacol 19(1):pyv072, pp. 1-7 doi:10.1093/ijnp/pyv072 (2015).
Dos Santos et al.: Antidepressive, anxiolytic, and antiaddictive effects of ayahuasca, psilocybin and lysergic acid diethylamide

(56) References Cited

OTHER PUBLICATIONS (LSD): a systematic review of clinical trials published in the last 25 years. Ther Adv Psychopharmacol. 6(3):193-213 doi:10.1177/2045125316638008 (2016).
Engelhardt, Eliasz, et al. Neuropsychiatric symptoms in brain diseases. Dement. Neuropsychol. 14(3):324-328 (2020).
EP Application No. 20748736.4 Extended European Search Report dated Aug. 9, 2022.
EP21848826.0 Extended European Search Report dated Jul. 15, 2024.
Erritzoe et al.: Effects of psilocybin therapy on personality structure. Acta Psychiatr Scand. 138(5):368-378 doi:10.1111/acps.12904 (2018).
Fadiman et al., Might microdosing psychedelics be safe and beneficial? An initial exploration. Journal of Psychoactive Drugs 51(2):118-122 (2019).
Family et al.: Safety, tolerability, pharmacokinetics, and pharmacodynamics of low dose lysergic acid diethylamide (LSD) in healthy older volunteers. Psychopharmacology (Berl). 237(3):841-853 doi:10.1007/s00213-019-05417-7 (2020).
Flanagan et al.: Psychedelics as anti-inflammatory agents. Int Rev Psychiatry. 30(4):363-375 doi:10.1080/09540261.2018.1481827 (2018).
GAD-7 Anxiety. Jun. 3, 2020; [retrieved on Jul. 22, 2024]. Available at URL: https://web.archive.org/web/20200603023323/https:/adaa.org/sites/default/files/GAD-7_Anxiety-updated_0.pdf p. 1.
Greenan et al., Preparation and characterization of novel crystalline solvates and polymorphs of psilocybin and identification of solid forms suitable for clinical development. Feb. 13, 2020 (Retrieved from https://www.researchgate.net/publication/33923871029).
Griffiths et al.: Psilocybin Occasioned Mystical-Type Experiences: Immediate and Persisting Dose-Related Effects. Psychopharmacology 218(4):649-665 (2011).
Griffiths et al.: Psilocybin Produces Substantial and Sustained Decreases in Depression and Anxiety in Patients With Life-threatening Cancer: A Randomized Double-blind Trial. Journal of Psychopharmacology 30(12):1181-1197 (2016).
Halberstadt et al.: Behavioral Neurobiology of Psychedelic Drugs. Springer 36:161 (2018).
Hasler et al.: Determination of psilocin and 4-hydroxyindole-3-acetic acid in plasma by HPLC-ECD and pharmacokinetic profiles of oral and intravenous psilocybin in man. Pharm Acta Helv. 72(3):175-184 (1997).
Hibicke et al. Psychedelics, but Not Ketamine, Produce Persistent Antidepressant-like Effects in a Rodent Experimental System for the Study of Depression. ACS Chem Neurosci. 11(6):864-871 (2020).
Higgins et al.: Low Doses of Psilocybin and Ketamine Enhance Motivation and Attention in Poor Performing Rats: Evidence for an Antidepressant Property. Front Pharmacol. 12:640241:1-19 doi:10.3389/fphar.2021.640241 (2021).
Higgins et al.: Rodent Test of Attention and Impulsivity: The 5-Choice Serial Reaction Time Task. Curr Protoc Pharmacol. 78:5.49.1-5.49.34 doi: 10.1002/cpph.27 (2017).
Hofmann, Albert et al. Psilocybin und Psilocin, zwei psychotrope Wirkstoffe aus mexikanischen Rauschpilzen. Helvetica Chimica Acta 42(5):1557-1572 (1959) (English Summary).
Hutten et al., Motives and side-effects of microdosing with psychedelics among users. International Journal of Neuropsychopharmacology. 22(7):426-434 (2019).
Hutten et al., Self-rated effectiveness of microdosing with psychedelics for mental and physical health problems among microdosers. Frontiers in Psychiatry. 10:1-9 (2019).
IV LSD experience reports. ResidentPurple, Reddit, Dec. 4, 2018; [retrieved on Jul. 22, 2024]. Available at https://www.reddit.com/r/LSD/comments/a2yrk1/IV_lsd_experience_reports p. 1.
Johns Hopkins Medicine, Obsessive-Compulsive Disorder. Retrieved from the Internet on Dec. 19, 2023: https://www.hopkinsmedicine.org/health/conditions-and-diseases/obsessivecompulsive-disorder.
Johnstad: Powerful substances in tiny amounts: An interview study of psychedelic microdosing. Nordisk Alkohol Nark 35(1):39-51 doi:10.1177/1455072517753339 (2018).
Kargbo, Robert B. et al. Direct Phosphorylation of Psilocin Enables Optimized cGMP Kilogram-Scale Manufacture of Psilocybin. ACS Omega 5(27):16959-16966 (2020).
Kryptonite: A Glorious New Year: LSD & MDMA (Ecstasy). Erowid, pp. 1-3 URL: https://erowid.org/experiences/exp.php?ID=58609 [retrieved online Jul. 29, 2022] (2009).
Lea et al., Perceived outcomes of psychedelic microdosing as self-managed therapies for mental and substance use disorders. Psychopharmacology 237:1521-1532 (2020).
Lee at al.: Combined effect of oleic acid and polyethylene glycol 200 on buccal permeation of [D-ala2, D-leu5]enkephalin from a cubic phase of glyceryl monooleate. Int J Pharm. 204(1-2):137-144 (2000).
Lindenblatt et al.: Quantitation of psilocin in human plasma by high-performance liquid chromatography and electrochemical detection: comparison of liquid-liquid extraction with automated on-line solid-phase extraction. J Chromatogr B Biomed Sci Appl. 709(2):255-263 doi:10.1016/s0378-4347(98)00067-x (1998).
Livescience, The weight of the world: Researchers weigh human population (2023) Retrieved from the Internet on Dec. 19, 2023: https://deserthopetreatment.com/addiction-guide/administration-methods/orally/.
Lopez-Gimenez et al.: Hallucinogens and Serotonin 5-HT 2A Receptor-Mediated Signaling Pathways. Curr Top Behav Neurosci. 36: 45-73 (2018).
Madsen et al.: Psychedelic effects of psilocybin correlate with serotonin 2A receptor occupancy and plasma psilocin levels. Neuropsychopharmacology 44(7):1328-1334 (2019).
Mahalingam et al.: Transbuccal delivery of 5-aza-2-deoxycytidine: effects of drug concentration, buffer solution, and bile salts on permeation. AAPS PharmSciTech 8(3):E55 [1-6] (2007).
Mental Health Conditions: Depression and Anxiety. Centers for Disease control and prevention, Web Archive, Dec. 31, 2019; [retrieved on Jul. 22, 2024]. Available at https://web.archive.org/web/20181231203416/https:/www.cdc.gov/tobacco/campaign/tips/diseases/depression-anxiety.html pp. 1-4.
Mertens et al., Therapeutic mechanisms of psilocybin: Changes in amygdala and prefrontal functional connectivity during emotional processing after psilocybin for treatment-resistant depression. Journal of Psychopharmacology 34(2):167-180 (2020).
Microdosing for Anxiety and Depression. Tetrisdroi, Erowid Experience Vaults, May 23, 2018; [retrieved on Jul. 22, 2024]. Available at URL:https://erowid.org/experiences/exp.php?ID=108178 pp. 1-2.
Moreno et al.: Safety, tolerability, and efficacy of psilocybin in 9 patients with obsessive-compulsive disorder. J Clin Psychiatry. 67(11):1735-1740 doi:10.4088/jcp.v67n1110 (2006).
Murray et al.: Low doses of LSD reduce broadband oscillatory power and modulate event-related potentials in healthy adults. Psychopharmacology (Berl) 239(6):1735-1747 doi:10.1007/s00213-021-05991-9 (2022).
Nagapudi et al.: Amorphous Active Pharmaceutical Ingredients in Preclinical Studies: Preparation, Characterization, and Formulation. Current Bioactive Compounds 400(4):213-224 doi:10.2174/157340708786847852 (2008).
Nichols, David E and Stewart Frescas. Improvements to the Synthesis of Psilocybin and a Facile Method for Preparing the O-Acetyl Prodrug of Psilocin. Synthesis 1999(6):935-938 (1999).
Nichols et al.: Serotonin Receptors. Chem. Rev. 108: 1614-1641 (2008).
Nicolazzo et al.: Modification of buccal drug delivery following pretreatment with skin penetration enhancers. J Pharm Sci. 93(8):2054-2063 (2004).
Nielson et al.: The Psychedelic Debriefing in Alcohol Dependence Treatment: Illustrating Key Change Phenomena through Qualitative Content Analysis of Clinical Sessions. Front Pharmacol. 9(132):1-13 doi:10.3389/fphar.2018.00132 (2018).
Passie: The Science of Microdosing Psychedelics: Microdosing Other Psychedelics. The Psychedelic Press, Chapter 15, pp. 199-206 ISBN 978-0992808884 (2019).
Passie, Torsten, et al. The pharmacology of lysergic acid diethylamide: A review. CNS Neurosci. Ther. 14(4):295-314 (2008).
Patient Health Questionnaire (PHQ-9). Pfizer Inc, Jun. 19, 2018; [retrieved on Jul. 22, 2024]. Available at URL: https://web.archive.

(56) References Cited

OTHER PUBLICATIONS org/web/20180619082559/https:/med.stanford.edu/fastlab/research/imapp/msrs/_jcr_content/main/accordion/accordion_content3/download_256324296/file.res/PHQ9%20id%20date%2008.03.pdf pp. 1-2.
PCT/IB2020/000052 International Search Report and Written Opinion dated Jun. 4, 2020.
PCT/IB2021/000488 International Search Report and Written Opinion dated Dec. 6, 2021.
PCT/IB2021/000494 International Search Report and Written Opinion dated Nov. 24, 2021.
PCT/IB2022/000103 International Search Report and Written Opinion dated Jul. 4, 2022.
PCT/IB2022/000513 International Search Report and Written Opinion dated Jan. 27, 2023.
PCT/IB2023/000349 International Search Report and Written Opinion dated Oct. 26, 2023.
Polito, Vince, and Richard J Stevenson. A systematic study of microdosing psychedelics. PLoS one 14(2):e0211023, 1-26 (2019).
Prochazkova, Luisa, et al., Exploring the Effect of Microdosing Psychedelics on Creativity in an Open-label Natural Setting. Psychopharmacology 235(12):3401-3413 (2018).
Rijckevorsel: Cognitive problems related to epilepsy syndromes, especially malignant epilepsies. Seizure 15(4):227-234 doi:10.1016/j.seizure.2006.02.019 (2006).
Ross et al.: Rapid and sustained symptom reduction following psilocybin treatment for anxiety and depression in patients with life-threatening cancer: a randomized controlled trial. J Psychopharmacol 30(12):1165-1180 doi:10.1177/0269881116675512 (2016).
Sakloth et al.: Effects of acute and repeated treatment with serotonin 5-HT2A receptor agonist hallucinogens on intracranial self-stimulation in rats. Exp Clin Psychopharmacol. 27(3):215-226 doi:10.1037/pha0000253 (2019).
Sandri et al.: Mucoadhesive and penetration enhancement properties of three grades of hyaluronic acid using porcine buccal and vaginal tissue, Caco-2 cell lines, and rat jejunum. J Pharm Pharmacol. 56(9):1083-1090 (2004).
Schenberg: Psychedelic-Assisted Psychotherapy: A Paradigm Shift in Psychiatric Research and Development. Front Pharmacol. 9(733):1-11 doi:10.3389/fphar.2018.00733 (2018).
Schott Lab 960 Conductivity Bench Laoratory Meter. CV Gihon Juma Sentosa, Jul. 18, 2024; [retrieved on Jul. 19, 2024]. Available at URL:https://en.gihonjumasentosa.com/product/schott-lab-960-conductivity-bench-laoratory-meter-p718127.aspx pp. 1-4.
Senel et al., Drug permeation enhancement via buccal route: possibilities and limitations. Journal of Controlled Release 72 (2001): 133-144.
Sercl et al.: Clinical Experiences with Psilocybin (CY 39 Sandoz). Psychiat Neurol. 142:137-146 doi:10.1159/000131157 (English Google Machine Translation included) (1961).
Sessa et al.: Underground MDMA-, LSD- and 2-CB-assisted individual and group psychotherapy in Zurich: Outcomes, implications and commentary. Drug Science, Policy and Law 2(0):1-8 (2015).
Sherwood, Alexander M. et al. An Improved, Practical, and Scalable Five-Step Synthesis of Psilocybin. Synthesis 52(5):688-694 (2020).
Shirota et al., Concise Large-Scale Synthesis of Psilocin and Psilocybin, Principal Hallucinogenic Constituents of "Magic Mushroom". J. Nat. Prod. 66(6):885-887 (2003).
Starokadomdkyy et al.: New absorption promoter for the buccal delivery: preparation and characterization of lysalbinic acid. Int J Pharm 308(1-2):149-154 (2006).
Sudhakar et al.: Buccal bioadhesive drug delivery—a promising option for orally less efficient drugs. J Control Release 114(1):15-40 (2006).
The Freelance Writer Using LSD for Depression. The Cut, Web Archive, Oct. 24, 2017; [retrieved on Jul. 22, 2024]. Available at URL:https://www.thecut.com/2017/10/microdosing-lsd-depression-coping-diaries.html pp. 1-3.
Timmermann et al.: Neural correlates of the DMT experience assessed with multivariate EEG. Sci Rep. 9(1):16324:1-13 doi:10.1038/s41598-019-51974-4 (2019).
U.S. Appl. No. 17/427,037 Notification of Third-Party Pre-Issuance Submission mailed Jul. 22, 2022.
U.S. Appl. No. 18/053,648 Final Office Action dated Apr. 24, 2023.
U.S. Appl. No. 18/053,648 Non-Final Office Action dated Mar. 7, 2023.
U.S. Appl. No. 62/574,307, filed Oct. 19, 2017.
U.S. Appl. No. 18/053,648 Office Action dated Apr. 30, 2024.
U.S. Appl. No. 18/053,648 Office Action dated Jan. 9, 2024.
U.S. Appl. No. 18/102,268 Notice of Third-party Submission dated Jan. 22, 2024.
Usona Institute, A randomized, double-blind, support-of-concept phase 2 study of single-dose psilocybin for major depressive disorder (MDD). Study record first posted Mar. 5, 2019. https://clinicaltrials.gov/study/NCT03866174.
Vaupel et al.: The inhibition of food intake in the dog by LDS, mescaline, psilocin, d-amphetamine and phenylisopropylamine derivatives. Life Sci. 24(26):2427-2431 doi:10.1016/0024-3205(79)90451-x (1979).
Voineskos et al., Management of treatment-resistant depression: Challenges and strategies. Neuropsychiatric Disease and Treatment 16:221-234 (2020).
Widder et al. Chapter 24: Theory and practice of Prodrugs Kinetics. Method in Enzymology. 112:309-396 (1985).
Xiuting et al.: Hallucinogenic Mushrooms: From God's Messenger to Human Medicine. Nanfang Daily, Edition 013, Medicine & Public Health, Newsweek Tech Visibility, pp. 1-3. China Academic Journal Electronic Publishing House. China Academic Journal Electronic Publishing House. [URL: http://www.cnki.net/KCMS/detail/detail.aspx?dbcode=CCND&dbname=CCNDLAST2014&filename=NFRB201409270130&uniplatform=OVERSEA&v=wDuBzelq46BeFwRM2MloyS-iDtu6ApnMcntTt8Tz2x-ebUksdocz3MTUOulTqKDNwEt9dTBajuo%3d] (Sep. 27, 2014).
Yaden et al., The Subjective Effects of Psychedelics are Necessary for Their Enduring Therapeutic Effects. ACS Pharmacol. Transl. Sci. 4(2): 568-572 (2021).
Banerjee, Emili, et al. Does serotonin deficit mediate susceptibility to ADHD? Neurochemistry International 82:52-68 (2015).
ClinicalTrials.gov. A Study of Psilocybin for Major Depressive Disorder (MDD). ClinicalTrials.gov Identifier: NCT03866174. First Posted Mar. 7, 2019. 11 pages. Search results downloaded on Jan. 8, 2024 from the Internet at URL: https://clinicaltrials.gov/study/NCT03866174.
Co-pending U.S. Appl. No. 18/812,812, inventors Blumstock; Judith et al., filed Aug. 22, 2024.
Co-pending U.S. Appl. No. 18/812,843, inventors blumstock; Judith et al., filed Aug. 22, 2024.
Co-pending U.S. Appl. No. 18/812,847, inventors Blumstock; Judith et al., filed Aug. 22, 2024.
Co-pending U.S. Appl. No. 18/813,959, inventors Blumstock; Judith et al., filed Aug. 23, 2024.
Co-pending U.S. Appl. No. 18/814,163, inventors Blumstock; Judith et al., filed Aug. 23, 2024.
Co-pending U.S. Appl. No. 18/814,172, inventors Blumstock; Judith et al., filed Aug. 23, 2024.
Co-pending U.S. Appl. No. 18/814,182, inventors Blumstock; Judith et al., filed Aug. 23, 2024.
Co-pending U.S. Appl. No. 19/030,518, inventors Blumstock; Judith et al., filed Jan. 17, 2025.
EP21848825.2 Extended European Search Report dated Nov. 6, 2024.
EP22766444.8 Extended European Search Report dated Dec. 23, 2024.
Greenan, Catherine, et al. Preparation and characterization of novel crystalline solvates and polymorphs of psilocybin and identification of solid forms suitable for clinical development. Published Feb. 13, 2020. DOI: 10.13140/RG.2.2.32357.14560, pp. 1-29.
Johns Hopkins Medicine, Health. Obsessive-Compulsive Disorder. Retrieved from the Internet on Dec. 19, 2023 (Year: 2023): https://www.hopkinsmedicine.org/health/conditions-and-diseases/obsessivecompulsive-disorder-ocd pp. 1-5.

(56) References Cited

OTHER PUBLICATIONS

Kuypers, Kim PC, et al. Microdosing psychedelics: More questions than answers? An overview and suggestions for future research. Journal of Psychopharmacology 33(9):1039-1057 (2019).
Psychedelic Science Review. Sandoz Parmaceutical Begins Selling Psilocybin Under the Trade Name Indocybin (2025) [retrieved on Feb. 27, 2025]. Available at URL: https://psychedelicreview.com/event/sandoz-parmaceutical-manufactures-indocybin/ pp. 1-4.
Rettner, Rachael. The Weight of the World: Researchers Weigh Human Population. Live Science, Future US Inc., New York, NY. Published May 30, 2013 (Year: 2023). Retrieved from the Internet on Dec. 19, 2023 at URL: https://www.livescience.com/36470-human-population-weight.html pp. 1-9. (Retrieved on Jan. 6, 2025. Retrieved from Internet (Wayback Machine): https://web.archive.org/web/20231004012405/https://www.livescience.com/36470-human-population-weight.html).
Rossa, Marley. Titrating your trip: Microdosing and mental health. Neuwrite San Diego, Apr. 12, 2018. Retrieved from the Internet: URL: https://neuwritesd.org/2018/04/12/titrating-your-trip-microdosing-and-mental-health/.
Sandison, R. A., et al. The Therapeutic Value of Lysergic Acid Diethylamide in Mental Illness. Journal of Mental Science 100(419):491-507 (1954).
Stielow, Marlena, et al. The Bioavailability of Drugs—The Current State of Knowledge. Molecules 28:8038 (2023) (19 pages).
U.S. Appl. No. 18/812,847 Office Action dated Jan. 16, 2025.
U.S. Appl. No. 18/813,959 Office Action dated Jan. 16, 2025.
U.S. Appl. No. 18/814,163 Office Action dated Nov. 29, 2024.
U.S. Appl. No. 18/814,163 Office Action dated Mar. 11, 2025.
U.S. Appl. No. 18/814,172 Office Action dated Jan. 3, 2025.
U.S. Appl. No. 18/814,182 Restriction Requirement dated Dec. 27, 2024.
Webster, Adrienne, LAC. Oral Drug Use: Signs, Effects & Types. Desert Hope Treatment Center. Updated: Nov. 14, 2022 (Year: 2023). Retrieved from the Internet on Dec. 19, 2023 at URL: https://deserthopetreatment.com/addiction-guide/administration-methods/orally/ pp. 1-5. (Retrieved on Jan. 6, 2025. Retrieved from Internet (Wayback Machine): https://web.archive.org/web/20230928004820/https://deserthopetreatment.com/addiction-guide/administration-methods/orally/).
Weston, Neil M., et al. Historic psychedelic drug trials and the treatment of anxiety disorders. Depression and Anxiety 37(12):1261-1279 (2020).
Catlow, Briony J. et al. Effects of psilocybin on hippocampal neurogenesis and extinction of trace fear conditioning. Experimental Brain Research 228(4):481-491 (2013).
Dittrich, A. The Standardized Psychometric Assessment of Altered States of Consciousness (ASCs) in Humans. Pharmacopsychiatry 31 (Suppl. 2):80-84 (1998).
Gasser, Peter et al. LSD-assisted psychotherapy for anxiety associated with a life-threatening disease: A qualitative study of acute and sustained subjective effects. Journal of Psychopharmacology 29(1):57-68 (2015).
Halberstadt, Adam L., et al. Behavioral Neurobiology of Psychedelic Drugs, vol. 36, Springer (434 pages) (2018).
Hasler et al. Acute psychological and physiological effects of psilocybin in healthy humans: a double-blind, placebo-controlled dose-effect study. Psychopharmacology (Berl). Mar. 2004;172(2):145-56. doi: 10.1007/s00213-003-1640-6. Epub Nov. 13, 2003.
Higgins, Guy A., et al. Low Doses of Psilocybin and Ketamine Enhance Motivation and Attention in Poor Performing Rats: Evidence for an Antidepressant Property. Frontiers in Pharmacology 12(640241) (2021), 19 pages.
Sekssaoui, Mehdi, et al. Antidepressant-like effects of psychedelics in a chronic despair mouse model: is the 5-HT2A receptor the unique player? Neuropsychopharmacology 49:747-756 (2024).
Studerus, Erich, et al. Acute, subacute and long-term subjective effects of psilocybin in healthy humans: A pooled analysis of experimental studies. J. Psychophamracol. 25:1434-1452 (2011).
Studerus, Erich, et al. Psychometric Evaluation of the Altered States of Consciousness Rating Scale (OAV). PLoS One 5(8):312412 (19 pages) (2010).
Weast, Robert C., Ph.D., et al., CRC Handbook of Chemistry and Physics, 70th Edition, 1989-1990, po. 8-228 (Year: 1989).
Yu, Lian. Amorphous pharmaceutical solids: preparation, characterization and stabilization. Advanced Drug Delivery Reviews 48(1):27-42 (2001).

* cited by examiner

| Sample | Reference |
|---|---|
| 7.05 | 7.02 |
| 4.86 | 4.91 |
| 3.33 | 3.30 |
| 2.91 | 2.87 |

AMORPHOUS (A-POLYMORPHIC) PSILOCYBIN

CROSS-REFERENCE

This application is a U.S. continuation application of the International Application No.: PCT/IB2023/000349, filed Jun. 8, 2023, which claims benefit of U.S. Provisional Patent Application No. 63/350,828 filed on Jun. 9, 2022, which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BACKGROUND OF THE INVENTION

Psilocybin is being explored for use in a number of therapeutic indications. Compositions comprising psilocybin, e.g, amorphous (e.g, a-polymorphic) psilocybin, are useful in treating such therapeutic indications. While there continues to be debate amongst researchers as to where the therapeutic window of psilocybin lies, it is generally understood that there is a narrow therapeutic window; under which therapeutic efficacy is not expected and above which undesired effects are expected.

SUMMARY OF THE INVENTION

In certain typical instances, psilocybin is used therapeutically in crystalline form. In some instances, crystalline morphologies of therapeutic agents can cause difficulties in achieving consistent and targeted therapeutic effects, pharmacokinetics, release rates, and the like. For example, in some instances, altering morphologies of therapeutic agents can cause the release and/or bioavailability of a therapeutic agent to increase or decrease. Such changing release rates can be problematic when targeting a narrow therapeutic window. There is therefore a need for an amorphous (e.g, a-polymorphic) psilocybin that is synthesized without producing psilocybin in crystalline form. Typically, it is expected that amorphous psilocybin concentrations present reduced physical stability and the psilocybin has a tendency to crystallize with time. Thus, there is a further need to provide stable amorphous psilocybin that provides the increased bioavailability of amorphous compositions while avoiding the typical stability and tendency to crystallize problems associated with amorphous compositions.

Provided in certain embodiments herein is amorphous (e.g, a-polymorphic) psilocybin, or psilocybin substantially free from crystalline psilocybin (e.g., less than 10 wt. %, less than 5 wt. %, less than 2 wt. %, less than 1 wt. %, or less than 1 wt. % crystalline psilocybin relative to total psilocybin). Provided in some embodiments herein are compositions (e.g., comprising a plurality of discrete particles), comprising (i) a carrier component; and (ii) a psilocybin component comprising amorphous (e.g, a-polymorphic) psilocybin. In some embodiments, the carrier component is optional. In some embodiments, the composition comprises a plurality of discrete particles, each of the plurality of discrete particles independently comprising at least a portion of the carrier component and at least a portion of the psilocybin component (e.g., as determined by X-ray powder diffraction (XRPD), melting point, differential scanning calorimetry (DSC), solid-state nuclear magnetic resonance (SSNMR), or polarized light microscopy). In some embodiments, at least 50 wt. % (e.g., 60 wt. % or more. 70 wt. % or more. 80 wt. % or more, or 90 wt. % or more) of the psilocybin component is amorphous (e.g, a-polymorphic) (e.g., as determined by XRPD, melting point, DSC, SSNMR, or polarized light microscopy). In some embodiments, one or more discrete particles of the plurality of discrete particles has a ratio of the carrier component to the psilocybin component that is about 1:99 to about 99:1 (e.g., about 1:99 to about 99:10, about 25:75 to about 75:25, about 40:60 to about 60:40, or about 40:60 to about 90:10, or about 80:20 to about 50:50) (e.g., on average). In some embodiments, each discrete particle of the plurality of discrete particles has a ratio of the carrier component to the psilocybin component that is about 1:99 to about 99:1 (e.g., about 1:99 to about 99:10, about 25:75 to about 75:25, about 40:60 to about 60:40, or about 40:60 to about 90:10, or about 80:20 to about 50:50) (e.g., on average). In some embodiments, the composition has a ratio of the carrier component to the psilocybin component that is about 1:99 to about 99:1 (e.g., about 1:99 to about 99:10, about 25:75 to about 75:25, about 40): 60 to about 60:40, or about 40:60 to about 90:10, or about 80:20 to 50:50) (e.g., on average). In some embodiments, at least one discrete particle of the plurality of discrete particles comprises at least one discrete domain embedded in a matrix. In some embodiments, at least one discrete particle of the plurality of discrete particles comprises a solid or semi-solid dispersion of psilocybin in a carrier component. In some embodiments, at least one discrete particle of the plurality of discrete particles comprises a solid or semi-solid solution of psilocybin in a carrier component. In some embodiments, the matrix comprises a portion of the carrier component and the discrete domain comprises a portion of the psilocybin component. In some embodiments, the matrix comprises a portion of the psilocybin component and the discrete domain comprises a portion of the carrier component. In some embodiments, the composition further comprises an additional agent selected from the group consisting of a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, tryptophan, lysergic acid diethylamide, or a 5HT receptor antagonist, and combinations thereof. In some embodiments, the composition is a pharmaceutical composition. In some embodiments, the pharmaceutical composition is suitable for oral administration. In some embodiments, wherein the composition is selected from the group consisting of a spray-dried composition, a freeze-dried composition, a drum-dried composition, a hot-melt extrusion composition, a precipitation composition (e.g, crash precipitation), a super critical fluidization composition and a pulse combustion dried composition. In some embodiments, wherein the composition is selected from the group consisting of a spray-dried composition, wet granulated/fluid bed dried composition, wet granuled/microwave dried composition, wet granuled/tray dried composition, a freeze-dried composition, a drum-dried composition, a hot-melt extrusion composition, a precipitation composition (e.g, crash precipitation), a super critical fluidization composition and a pulse combustion dried composition. In some embodiments, the composition is a spray-dried composition or a hot-melt extrusion composition. In some embodiments, at least a portion of the carrier component is selected from the group consisting of acacia, gelatin, colloidal silicon dioxide, calcium glycerophosphate, calcium lactate, maltodextrin, glycerin, magnesium silicate, polyvinylpyrrolidone (PVP), polyvinyl pyrrolidone-co-vinyl acetate, polyacrylic acid (PAA), polyvinyl alcohol, hydroxypropyl methylcellulose acetate succinate (HPMCAS), poly(ethylene glycol-propylene glycol-ethylene glycol)triblock copolymers, cholesterol, cholesterol esters, sodium caseinate, soy lecithin, taurocholic acid, phosphatidylcholine, sodium chloride, tricalcium phosphate, dipotassium phosphate, cellulose (e.g., a cellulose conjugate), sugars sodium stearoyl lactylate, carrageenan, monoglyceride, diglyceride, polyethylene glycol (PEG), hydroxypropyl methylcellulose (HPMC), and pregelatinized starch. In some embodiments, the psilocybin component is substantially free of crystalline psilocybin (e.g., as determined by XRPD, melting point. DSC. SSNMR, or polarized light microscopy). In some embodiments, the psilocybin component is entirely free of crystalline psilocybin (e.g., as determined by XRPD, melting point. DSC. SSNMR, or polarized light microscopy).

The present disclosure also provides for a plurality of discrete particles, comprising (i) a carrier component comprising at least one carrier; and (ii) a psilocybin component comprising amorphous (e.g, a-polymorphic) psilocybin (e.g., as determined by XRPD. DSC, melting point, SSNMR, or polarized light microscopy). In some embodiments, at least one discrete particle comprises at least one discrete domain embedded in a matrix, the matrix comprising a portion of the carrier component and the discrete domain comprising a portion of the psilocybin component.

In some embodiments, at least one discrete particle comprises at least one discrete domain embedded in a matrix, the matrix comprising a portion of the psilocybin component and the discrete domain comprising a portion of the carrier component. In some embodiments, each of the plurality of discrete particles comprise (i) at least a portion of the carrier component and (ii) at least a portion of the psilocybin component. In some embodiments, the plurality of discrete particles is selected from the group consisting of spray-dried particles, freeze-dried particles, drum dried particles, hot-melt extrusion particles, precipitation particles (e.g, crash precipitation), super critical fluidization particles and pulse combustion dried particles. In some embodiments, the plurality of discrete particles is selected from the group consisting of spray-dried particles, wet granuled/fluid bed dried particles, wet granuled/microwave dried particles, wet granuled/tray dried particles, freeze-dried particles, drum dried particles, hot-melt extrusion particles, precipitation particles (e.g, crash precipitation), super critical fluidization particles and pulse combustion dried particles. In some embodiments, one or more discrete particle of the plurality of discrete particles has a ratio of the carrier component to the psilocybin component that is about 1:99 to about 99:1 (e.g., about 1:99 to about 99:10, about 25:75 to about 75:25 or about 40:60 to about 60:40, or 40:60 to about 90:10, or about 80:20 to 50:50) (e.g., on average). In some embodiments, each particle of the plurality of discrete particles has a ratio of the carrier component to the psilocybin component of about 1:99 to about 99:1 (e.g., about 1:99 to about 99:10, about 25:75 to about 75:25 or about 40:60 to about 60:40, or about 40:60 to about 90:10, or about 80:20 to 50:50) (e.g., on average). In some embodiments, at least one discrete particle of the plurality of discrete particles comprises a solid or semi-solid dispersion of psilocybin in a carrier component. In some embodiments, at least one discrete particle of the plurality of discrete particles comprises a solid or semi-solid solution of psilocybin in a carrier component. In some embodiments, at least a portion of the carrier component is selected from the group consisting of acacia, gelatin, colloidal silicon dioxide, calcium glycerophosphate, calcium lactate, maltodextrin, glycerin, magnesium silicate, polyvinylpyrrolidone (PVP), polyvinyl pyrrolidone-co-vinyl acetate, polyacrylic acid (PAA), polyvinyl alcohol, hydroxypropyl methylcellulose acetate succinate (HPMCAS), poly (ethylene glycol-propylene glycol-ethylene glycol)triblock copolymers, cholesterol, cholesterol esters, sodium caseinate, soy lecithin, taurocholic acid, phosphatidylcholine, sodium chloride, tricalcium phosphate, dipotassium phosphate, cellulose (e.g., a cellulose conjugate), sugars sodium stearoyl lactylate, carrageenan, monoglyceride, diglyceride, polyethylene glycol (PEG), hydroxypropyl methylcellulose (HPMC), and pregelatinized starch. In some embodiments, the plurality of discrete particles further comprises an additional agent selected from the group consisting of a stimulant, an antihistamine, an antiemetic, an antidepressant, an anti-inflammatory, a growth factor, a lithium compound, resveratrol, phosphatidylcholine, curcumin, magnesium, melatonin, pregnenolone. ginseng, tryptophan, lysergic acid diethylamide, or a 5HT receptor antagonist, and combinations thereof. In some embodiments, at least 50 wt. % or more (e.g., 60 wt. % or more. 70 wt. % or more. 80 wt. % or more, or 90 wt. % or more) of the psilocybin component is amorphous (e.g, a-polymorphic) psilocybin (e.g., as determined by XRPD, melting point. DSC. SSNMR or polarized light microscopy). In some embodiments, at most a portion of the psilocybin has a crystallinity of at most 10% (e.g., 10% or less. 8% or less. 6% or less. 5% or less, or 4% or less. 2% or less, or 1% or less) (e.g., as determined by XRPD. DSC, melting point. SSNMR, or polarized light microscopy). In some embodiments, the psilocybin component is substantially free of crystalline psilocybin (e.g., as determined by XRPD, melting point. DSC. SSNMR, or polarized light microscopy). In some embodiments, the psilocybin component is entirely free of crystalline psilocybin (e.g., as determined by XRPD, melting point. DSC. SSNMR, or polarized light microscopy).

The present disclosure also provides a method for treating a mental, a behavioral, or a neuropsychiatric condition, and/or symptoms thereof, in an individual (e.g., in need thereof), the method comprising (e.g., orally) administering to the individual (e.g., in need thereof) any composition (e.g., a plurality of discrete particles) as disclosed herein. In some embodiments, the mental, the behavioral, or the neuropsychiatric condition is an attention condition or a cognitive (e.g., neurocognitive) condition. In some embodiments, the mental, the behavioral, or the neuropsychiatric condition (e.g., a Diagnostic and Statistical Manual of Mental Disorders (DSM-5) category or non-DSM-5 category disease or disorder) is induced by stress and/or anxiety. In some embodiments, the mental, the behavioral, or the neuropsychiatric condition (e.g., a DSM-5 category or non-DSM-5 category disease or disorder) is selected from the group consisting of addiction, anxiety (e.g., post-traumatic stress disorder (PTSD), constructive impulsivity, a phobia, or fear), apathy, and depression (e.g., major depressive disorder). In some embodiments, the symptoms of the mental, a behavioral, or a neuropsychiatric condition are physical, behavioral, emotional, mental, or a combination thereof. In some embodiments, the attention condition is attention deficit hyperactivity disorder (ADHD) or attention deficit disorder (ADD). In some embodiments, the cognitive condition is mild cognitive impairment, dementia, or Alzheimer's disease.

The present disclosure also provides a method for producing amorphous (e.g, a-polymorphic) psilocybin, the method comprising (i) providing (e.g., synthesizing) a psilocybin component. (ii) combining the psilocybin component with a carrier component, the carrier component comprising at least one carrier to produce a psilocybin-carrier composition; and (iii) processing the psilocybin-carrier composition to produce (e.g., an amorphous composition comprising) one or more particles comprising the amorphous (e.g, a-polymorphic) psilocybin (e.g., component) and the carrier component. In some embodiments, processing is selected from the group consisting of spray drying, wet granulation/fluid bed drying, wet granulation/microwave dying, wet granulation/tray drying, freeze drying, drum drying, precipitating (e.g, crash precipitation), hot-melt extrusion, super critical fluidization and pulse combustion drying. In some embodiments, processing is spray drying. In some embodiments, processing is hot-melt extrusion.

The present disclosure also provides a method for producing an amorphous composition comprising psilocybin, the method comprising (i) synthesizing a psilocybin component; and (ii) producing an amorphous composition comprising the psilocybin component. In some embodiments, processing is selected from the group consisting of spray drying, freeze drying, drum drying, precipitating (e.g, crash precipitation), hot-melt extrusion, super critical fluidization and pulse combustion drying. In some embodiments, processing is spray drying. In some embodiments, processing is hot-melt extrusion. In some embodiments, the amorphous (e.g, a-polymorphic) psilocybin is substantially free of crystalline psilocybin (e.g., as determined by XRPD, melting point. DSC. SSNMR, or polarized light microscopy). In some embodiments, the psilocybin component is entirely free of crystalline psilocybin (e.g., as determined by XRPD, melting point. DSC, SSNMR, or polarized light microscopy). In some embodiments, the synthesizing step produces an amorphous (e.g, a-polymorphic) psilocybin component that is entirely free of crystalline psilocybin (e.g., as determined by XRPD, melting point. DSC. SSNMR, or polarized light microscopy) (e.g. XRPD scan is free of reflexes or peaks). In some embodiments, the synthesizing does not include a crystallization step (e.g, of psilocybin). In some embodiments, the synthesizing step produces a psilocybin component that has a chemical purity of at least 95% (e.g. at least 95%, 96%, 97%, 98%, 99% or 99.5% and all values therebetween), as determined by, e.g. High Performance Liquid Chromatography (HPLC), with no single impurity greater that 2% (e.g. less than 2%, less than 1%, less than 0.5%, less than 0.15%). In some embodiments, at least 50 wt. % (e.g., 60) wt. % or more. 70 wt. % or more. 80 wt. % or more, or 90 wt. % or more) of the psilocybin component is amorphous (e.g, a-polymorphic) psilocybin (e.g., as determined by XRPD, melting point. DSC. SSNMR, or polarized light microscopy). In some embodiments, wherein at least one particle of the one or more particles comprises a solid or semi-solid dispersion of psilocybin in a carrier component. In some embodiments, at least one particle of the one or more particles comprises a solid or semi-solid solution of psilocybin in a carrier component. In some embodiments, the psilocybin component comprises amorphous (e.g, a-polymorphic) psilocybin. In some embodiments, at least a portion of the carrier component is selected from the group consisting of acacia, gelatin, colloidal silicon dioxide, calcium glycerophosphate, calcium lactate, maltodextrin, glycerin, magnesium silicate, polyvinylpyrrolidone (PVP), polyvinyl pyrrolidone-co-vinyl acetate, polyacrylic acid (PAA), polyvinyl alcohol, hydroxypropyl methylcellulose acetate succinate (HPMCAS), poly(ethylene glycol-propylene glycol-ethylene glycol)triblock copolymers, cholesterol, cholesterol esters, sodium caseinate, soy lecithin, taurocholic acid, phosphatidylcholine, sodium chloride, tricalcium phosphate, dipotassium phosphate, cellulose (e.g., a cellulose conjugate), sugars sodium stearoyl lactylate, carrageenan, monoglyceride, diglyceride, polyethylene glycol (PEG), hydroxypropyl methylcellulose (HPMC), and pregelatinized starch.

Provided herein in some embodiments, is a composition (e.g., an amorphous composition) produced by any of the methods described herein. In some embodiments, the differential scanning calorimetry (DSC) is modulated DSC.

Provided herein in some embodiments is a method for producing an amorphous composition comprising psilocybin, the method comprising: (i) synthesizing a psilocybin component; and (ii) producing an amorphous composition comprising the psilocybin component.

In some embodiments, producing comprises spray drying, wet granulated/fluid bed drying, wet granulated/microwave drying, wet granulated/tray drying, freeze drying (e.g., lyophilization), drum drying, precipitating (e.g, crash precipitation), hot-melt extrusion, super critical fluidization or pulse combustion drying. In some embodiments, producing comprises spray drying. In some embodiments, producing comprises lyophilization. In some embodiments, the lyophilization or spray drying is conducted in the absence of a carrier (e.g, polymer). In some embodiments, producing comprises lyophilization or spray drying in the presence of one or more sugars. In some embodiments, the one or more sugars comprise mannitol and/or trehalose. In some embodiments, the spray drying comprises spray drying in the presence of silicon dioxide.

In some embodiments, the psilocybin component is the only component of the amorphous composition.

In some embodiments, the amorphous composition is entirely free of crystalline psilocybin (e.g., as determined by XRPD, melting point. DSC (e.g, modulated DSC). SSNMR, or polarized light microscopy). In some embodiments, the psilocybin component is entirely free of crystalline psilocybin (e.g., as determined by XRPD, melting point. DSC (e.g, modulated DSC). SSNMR, or polarized light microscopy). In some embodiments, the synthesizing provides a-polymorphic psilocybin that is entirely free of crystalline psilocybin (e.g., as determined by XRPD, melting point. DSC (e.g, modulated DSC). SSNMR, or polarized light microscopy) (e.g. XRPD scan is free of reflexes or peaks). In some embodiments, the synthesizing does not include a crystallization step (e.g, of psilocybin). In some embodiments, the producing provides a-polymorphic psilocybin that is entirely free of crystalline psilocybin (e.g., as determined by XRPD, melting point. DSC (e.g, modulated DSC). SSNMR, or polarized light microscopy) (e.g. XRPD scan is free of reflexes or peaks).

In some embodiments, the synthesizing provides a psilocybin component that has a chemical purity of at least 95% (e.g, at least 95%, 96%, 97%, 98%, 99% or 99.5% and all values therebetween), as determined by, e.g. High Performance Liquid Chromatography (HPLC) or Reverse-Phase HPLC, with no single impurity greater that 2% (e.g, less than 2%, less than 1%, less than 0.5%, less than 0.15%). In some embodiments, the producing provides a psilocybin component that has a chemical purity of at least 95% (e.g, at least 95%, 96%, 97%, 98%, 99% or 99.5% and all values therebetween), as determined by, e.g. High Performance Liquid Chromatography (HPLC) or Reverse-Phase HPLC, with no single impurity greater that 2% (e.g. less than 2%, less than 1%, less than 0.5%, less than 0.15%). In some embodiments, at least 25 wt. % 50 wt. % (e.g., 60 wt. % or more. 70 wt. %. 75 wt. % or more, 80 wt. % or more, or 90 wt. % or more) of the amorphous composition is a-polymorphic psilocybin (e.g., as determined by XRPD, melting point. DSC (e.g, modulated DSC). SSNMR, or polarized light microscopy). In some embodiments, the psilocybin component consists of amorphous (e.g., a-polymorphic) psilocybin.

In some embodiments, the amorphous composition is not a dispersion (e.g, solid).

Provided herein is a composition (e.g., an amorphous composition) produced by any one of the claims provided herein.

Provided herein is a synthetic, a-polymorphic psilocybin composition that is entirely free of crystalline psilocybin (e.g., as determined by XRPD, melting point. DSC (e.g, modulated DSC). SSNMR, or polarized light microscopy). In some embodiments, the synthetic, a-polymorphic psilocybin has a chemical purity of at least 95% (e.g, at least 95%, 96%, 97%, 98%, 99% or 99.5% and all values therebetween), as determined by, e.g. High Performance Liquid Chromatography (HPLC) or Reverse-Phase HPLC, with no single impurity greater that 2% (e.g, less than 2%, less than 1%, less than 0.5%, less than 0.15%). In some embodiments, the synthetic, a-polymorphic psilocybin has a chemical purity of at least 98%.

In some embodiments, the synthetic, a-polymorphic psilocybin is concentrated. In some embodiments, the concentrated synthetic, a-polymorphic psilocybin composition is a spray-dried a-polymorphic psilocybin composition. In some embodiments, the concentrated synthetic, a-polymorphic psilocybin composition is a lyophilized a-polymorphic psilocybin composition. In some embodiments, the synthetic, a-polymorphic psilocybin further comprises one or more sugars (e.g, mannitol, trehalose). In some embodiments, the synthetic, a-polymorphic psilocybin further comprises silicon dioxide.

In some embodiments, the a-polymorphic psilocybin composition is carrier-free (e.g, free of polymers). In some embodiments, the a-polymorphic psilocybin composition is not a dispersion (e.g, solid). In some embodiments, the a-polymorphic psilocybin composition is carrier-free (e.g. free of polymers) and is entirely free of crystalline psilocybin following 1-2 weeks of storage at controlled RT (e.g., as determined by XRPD, melting point, DSC (e.g, modulated DSC), SSNMR, or polarized light microscopy).

Provided herein, in some embodiments, is a method of making a synthetic, a-polymorphic psilocybin composition, the method comprising: (a) providing psilocybin: (b) deprotecting the protected psilocybin in a reaction solvent to provide psilocybin: (c) extracting the psilocybin from the reaction solvent into an aqueous medium and washing the aqueous medium with an organic solvent: (d) concentrating the aqueous medium comprising the psilocybin; and (e) collecting the amorphous (e.g, a-polymorphic) psilocybin.

In some embodiments, at least 50% (e.g., at least 60%, at least 70%, at least 80%, at least 90%, at least 95%, at least 97%, at least 99%, at least 99.5%) of the composition is comprised of the amorphous psilocybin.

In some embodiments, the protected psilocybin is represented by the structure:

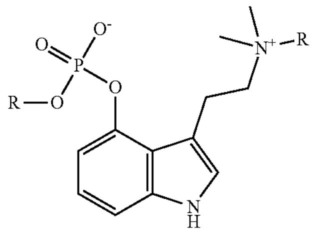

In some embodiments, each R is independently hydrogen or a protecting group.

In some embodiments, both R are protecting groups. In some embodiments, the protecting group comprises benzene. In some embodiments, both R are Hydrogen. In some embodiments, the protecting group is methylbenzene.

In some embodiments, deprotecting comprises hydrogenolysis. In some embodiments, the reaction solvent comprises an alcohol. In some embodiments, the reaction solvent comprises methanol. In some embodiments, the organic solvent comprises a halocarbon. In some embodiments, the organic solvent comprises dichloromethane. In some embodiments, the aqueous medium has a pH of about 9.

In some embodiments, concentrating comprises spray drying. In some embodiments, concentrating comprises lyophilizing. In some embodiments, the method does not require distillation of the aqueous medium. In some embodiments, the synthetic, a-polymorphic psilocybin composition is at least 98% pure without the need for crystallization.

Provided herein, in some embodiments, is a pure, synthetic a-polymorphic psilocybin produced by any one of the methods provided herein.

In some embodiments, provided herein is a composition, wherein at least 50% of the composition is comprised of amorphous psilocybin.

In some embodiments, at least 60% (e.g., at least 70%, at least 80%, at least 90%, at least 95%, at least 97%, at least 99%, at least 99.5%) of the composition is comprised of the amorphous psilocybin. In some embodiments, the amorphous psilocybin is at least 10% amorphous (e.g., at least 20% amorphous, at least 25% amorphous, at least 40% amorphous, at least 50% amorphous, least 60% amorphous, at least 75% amorphous, at least 80% amorphous, at least 90% amorphous, at least 95% amorphous, at least 96% amorphous, at least 97% amorphous, at least 98% amorphous, at least 99% amorphous) (e.g., as measured by power x-ray diffraction (XRPD)). In some embodiments, the amorphous psilocybin is present in the composition at a purity of at least 85% (e.g., at least 90%, at least 95%, at least 97%, at least 98%, at least 99%, at least 99.5%). In some embodiments, the composition comprises a polymer in an amount of less than 20% (e.g., less than 40%, less than 30%, less than 10%, less than 5%, less than 2.5%, less than 1%). In some embodiments, the amorphous psilocybin is not dispersed throughout a polymer matrix.

In some embodiments, the composition is (e.g., physically and/or chemically) stable for at least 1 week (e.g, at least 30 days, at least 60 days, at least 90 days, at least 6 months, at least 1 year) (e.g., at ambient conditions).

In some embodiments, the psilocybin has never been crystalline (e.g., as determined by powder x-ray diffraction (XRPD)).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION OF THE INVENTION

Certain Definitions

Figure 1:
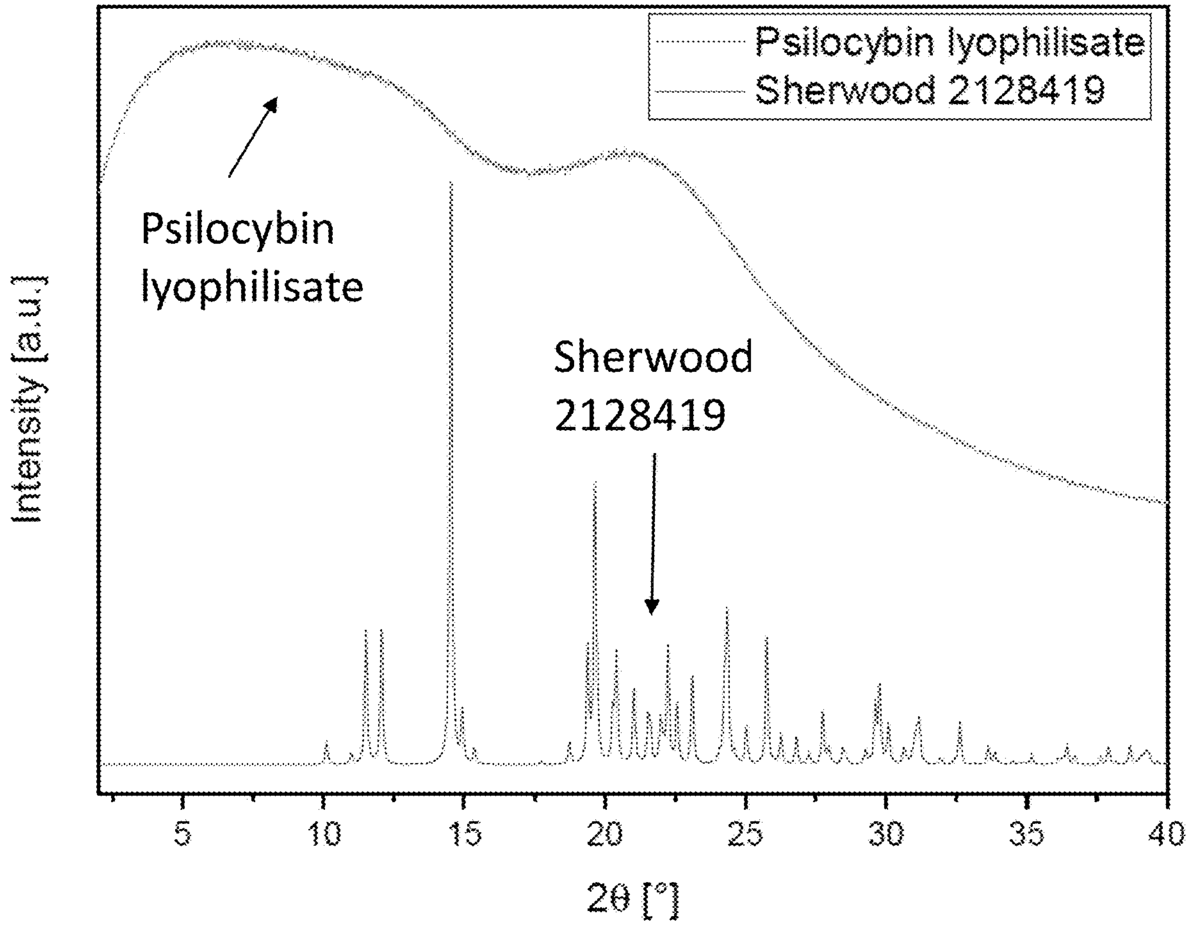
FIG. 1 illustrates the XRPD of psilocybin lyophilisate compared to a reference spectrum (Sherwood 2128419, from the Cambridge Structural Database).

As used herein and in the appended claims, the singular forms "a." "and." and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The term "entirely free" as used herein, means comprising less than 0.01%. 0.02%. 0.03%. 0.04%. 0.05%. 0.06%. 0.07%. 0.08%. 0.09%. 0.1%. 0.2%. 0.3%, or 0.5% or an undetectable amount of a property (e.g., crystallinity) or a substance (e.g., an impurity). The term "entirely" as used herein, means comprising at least 99.99%, 99.9%, 99.8%, 99.7%, or 99.5% of a property (e.g., crystallinity or lack thereof) or substance (e.g., psilocybin).

The terms "treat." "treating." or "treatment" as used herein, include reducing, alleviating, abating, ameliorating, managing, relieving, or lessening the symptoms associated with a disease, disease state, condition, or indication (e.g., provided herein) in either a chronic or acute therapeutic scenario. Also, treatment of a disease or disease state described herein includes the disclosure of use of such compound or composition for the treatment of such disease, disease state, disorder, or indication.

The terms "effective amount" or "pharmaceutically effective amount" or "therapeutically effective amount" refer to a nontoxic but sufficient amount of the agent to provide the desired biological, therapeutic, and/or prophylactic result. That result might be reduction and/or alleviation of the signs, symptoms, or causes of a disease, or any other desired alteration of a biological system. For example, an "effective amount" for therapeutic uses is the amount of a composition or plurality of discrete particles disclosed herein required to provide a clinically significant decrease in a disease or disorder. An appropriate effective amount in any individual case might be determined by one of ordinary skill in the art using routine experimentation.

"Solubility" generally means the amount of a compound dissolved in a solvent. Suitable solvents include aqueous and non-aqueous solvents.

"Poor solubility" means a small amount of compound dissolved in a solvent. Poor solubility is not an absolute term, but depends on the amount of the compound that is needed for effective treatment of a disease or condition. A compound will be poorly soluble if its solubility is lower than is desired in order for an effective treatment of a disease or condition.

"Enhanced solubility" means higher solubility than for a 5HT receptor agonist or a pharmaceutically acceptable salt, solvate, metabolite, derivative, or prodrug thereof alone. Enhanced solubility in water can be useful because many bodily fluids such as blood are water based (aqueous) and therefore, a more water soluble drug might have higher bioavailability. While the exact solubility of a compound in pure water is not the same as in an aqueous solution such as blood, a composition's solubility in pure water is often a good indication of solubility in other aqueous solutions.

"Particle" means a particle or body of any size or shape, including large particles (e.g., such as those produced by hot-melt extrusion) and small particles (e.g., such as those produced by spray-drying or by wet granulation/fluid, microwave or tray drying)).

Amorphous Psilocybin

Provided in some embodiments herein is a (e.g., solid (e.g., semi-solid (e.g., amorphous)) or liquid) composition (e.g., comprising a plurality of discrete particles), comprising amorphous (e.g., a-polymorphic) psilocybin (e.g., as determined by X-ray powder diffraction (XRPD), differential scanning calorimetry (DSC) (e.g., modulated DSC), melting point, solid-state nuclear magnetic resonance (SSNMR), or polarized light microscopy).

In some embodiments, provided herein is a composition (e.g., solid (e.g., semi-solid (e.g., amorphous)) or liquid) comprising a psilocybin component. In some embodiments, the amorphous psilocybin is synthesized without producing a crystalline (e.g, psilocybin) intermediary (an a-polymorphic psilocybin). In some embodiments, the psilocybin component comprises amorphous (e.g., a-polymorphic) psilocybin. In some embodiments, the composition comprises a carrier component. In some embodiments, provided herein is a composition, comprising a carrier component and a psilocybin component.

Provided in some embodiments herein is a composition, comprising a carrier component and a psilocybin component. Further provided in some embodiments herein is a plurality of discrete particles comprising a carrier component and a psilocybin component. In some embodiments, the psilocybin component comprises amorphous (e.g., a-polymorphic) psilocybin.

In some embodiments, any one of the compositions (e.g., psilocybin compositions) provided herein is an (e.g., synthetic) a-polymorphic psilocybin composition. In some embodiments, provided herein are a-polymorphic psilocybin compositions. In some embodiments, the a-polymorphic psilocybin compositions provided herein are synthetic, a-polymorphic psilocybin compositions. In some embodiments, the a-polymorphic psilocybin compositions are (e.g., entirely) free of natural components (e.g, mushroom extracts). In some embodiments, the a-polymorphic psilocybin compositions are (e.g., entirely) free of crystalline psilocybin. In some embodiments, the synthetic, a-polymorphic psilocybin compositions are (e.g., entirely) free of crystalline psilocybin. Provided herein in some embodiments is a synthetic, a-polymorphic psilocybin composition that is entirely free of crystalline psilocybin (e.g., as determined by XRPD, melting point. DSC (e.g., modulated DSC). SSNMR, or polarized light microscopy). In some embodiments, the a-polymorphic psilocybin compositions are (e.g., substantially) free of crystalline psilocybin. In some embodiments, the synthetic, a-polymorphic psilocybin compositions are (e.g., substantially) free of crystalline psilocybin. In some embodiments, provided herein is a synthetic, a-polymorphic psilocybin composition that is substantially free of crystalline psilocybin (e.g., as determined by XRPD, melting point. DSC (e.g., modulated DSC). SSNMR, or polarized light microscopy). In some embodiments, the psilocybin component is the only component of the amorphous composition.

Provided in some embodiments herein is a composition produced by any one of the methods provided herein. In some embodiments, the composition produced by any one of the methods provided herein is an amorphous composition. In some embodiments, the composition is an amorphous psilocybin composition. In some embodiments, the composition is an a-polymorphic psilocybin composition.

In some embodiments, the psilocybin (e.g., a-polymorphic psilocybin) composition provided herein is concentrated. In some embodiments, the psilocybin (e.g., a-polymorphic psilocybin) composition provided herein is a spray dried psilocybin (e.g., a-polymorphic psilocybin) composition. In some embodiments, the psilocybin (e.g., a-polymorphic psilocybin) composition provided herein is a lyophilized psilocybin (e.g., a-polymorphic psilocybin) composition.

In some embodiments, provided herein is a composition (e.g., (e.g., synthetic) a-polymorphic composition or amorphous psilocybin composition) wherein at least 50% of the composition is comprised of amorphous (e.g., a-polymorphic) psilocybin. In some embodiments, provided herein is a composition (e.g., (e.g., synthetic) a-polymorphic composition or amorphous psilocybin composition) wherein at least 50% (at least 60%, at least 70%, at least 80%, at least 90%, at least 95%, at least 97%, at least 99%) of the composition is comprised of amorphous (e.g., a-polymorphic) psilocybin. In some embodiments, provided herein is a composition (e.g., (e.g., synthetic) a-polymorphic composition or amorphous psilocybin composition) wherein at most 99.5% (e.g., at most 99%, at most 98.5%, at most 97%, at most 95%, at most 90%, at most 80%, at most 70%, at most 60%) of the composition comprises psilocybin.

In some embodiments, the composition comprises a psilocybin (e.g., amorphous (e.g., a-polymorphic) psilocybin) component. In some embodiments, a discrete particle of a plurality of discrete particles comprises a psilocybin (e.g., amorphous (e.g., a-polymorphic) psilocybin) component. In some embodiments, the plurality of discrete particles comprises a psilocybin (e.g., amorphous (e.g., a-polymorphic) psilocybin) component. In some embodiments, the psilocybin component comprises psilocybin. In some embodiments, the psilocybin component comprises psilocin. In some embodiments, the psilocybin component comprises psilocybin and psilocin. In some embodiments, the psilocybin component comprises amorphous psilocin.

In some embodiments, in any one of the compositions provided herein, the a-polymorphic psilocybin has never been crystalline, such as at any point during production of the psilocybin. In some embodiments, in any one of the compositions provided herein, the a-polymorphic psilocybin has never been substantially crystalline, such as at any point during production of the psilocybin. In some instances, a-polymorphic psilocybin can take the form of multiple different crystalline states, but the a-polymorphic psilocybin compositions provided herein have never been in any of those crystalline states.

In some embodiments, the composition consists essentially of amorphous (e.g., a-polymorphic) psilocybin. In some embodiments, the composition is substantially free (e.g., less than 10 wt. %, less than 8 wt. %, less than 6 wt. %, less than 4 wt. %, less than 2 wt. % or less than 1 wt. %) of crystalline psilocybin (e.g., as determined by XRPD, melting point. DSC (e.g., modulated DSC). SSNMR, or polarized light microscopy).

In some embodiments, in any of the compositions provided herein, at least 25 wt. % (e.g., 50) wt. % or more. 60 wt. % or more. 70 wt. % or more. 75 wt. % or more. 80 wt. % or more, or 90 wt. % or more) of the amorphous (e.g., a-polymorphic) psilocybin composition is amorphous (a-polymorphic) psilocybin. In some embodiments, in any of the compositions provided herein, at most 90 wt. % (e.g., at most 80 wt. %, at most 75 wt. %, at most 50 wt. %, at most 30 wt. %, at most 25 wt. %) of the amorphous (e.g., a-polymorphic) psilocybin composition is amorphous (e.g., a-polymorphic) psilocybin. In some embodiments, about 25 wt. % to about 90 wt. % of the amorphous (e.g., a-polymorphic) psilocybin composition is amorphous (e.g., a-polymorphic) psilocybin.

In some embodiments, the plurality of discrete particles consists essentially of amorphous (e.g., a-polymorphic) psilocybin. In some embodiments, the plurality of discrete particles is substantially free (e.g., less than 10 wt. %, less than 8 wt. %, less than 6 wt. %, less than 4 wt. %, less than 2 wt. % or less than 1 wt. %) of crystalline psilocybin (e.g., as determined by XRPD, melting point. DSC. SSNMR, or polarized light microscopy).

In some embodiments, the psilocybin component is substantially free (e.g., less than 10 wt. %, less than 8 wt. %, less than 6 wt. %, less than 4 wt. %, less than 2 wt. % or less than 1 wt. %) of crystalline psilocybin (e.g., as determined by XRPD, melting point. DSC. SSNMR, or polarized light microscopy). In some embodiments, the amorphous (e.g., a-polymorphic) psilocybin is substantially free (e.g., less than 10 wt. %, less than 8 wt. %, less than 6 wt. %, less than 4 wt. %, less than 2 wt. % or less than 1 wt. %) of crystalline psilocybin (e.g., as determined by XRPD, melting point. DSC. SSNMR, or polarized light microscopy).

In some instances, the composition comprises an amount of crystalline psilocybin that is at most 10 wt. % (e.g., 10 wt. % or less. 8 wt. % or less. 6 wt. % or less. 4 wt. % or less. 2 wt. % or less, or 1 wt. % or less) (e.g., as determined by XRPD, melting point. DSC. SSNMR, or polarized light microscopy). In some instances, the psilocybin component comprises an amount of crystalline psilocybin that is at most 10 wt. % (e.g., 10 wt. % or less. 8 wt. % or less. 6 wt. % or less. 4 wt. % or less. 2 wt. % or less, or 1 wt. % or less) (e.g., as determined by XRPD, melting point. DSC. SSNMR, or polarized light microscopy). In some embodiments, the composition is entirely free of crystalline psilocybin (e.g., as determined by XRPD, melting point. DSC. SSNMR, or polarized light microscopy). In some embodiments, the psilocybin component is entirely free of crystalline psilocybin (e.g., as determined by XRPD, melting point. DSC. SSNMR, or polarized light microscopy).

In some instances, the plurality of discrete particles comprises an amount of crystalline psilocybin that is at most 10 wt. % (e.g., 10 wt. % or less. 8 wt. % or less. 6 wt. % or less. 4 wt. % or less. 2 wt. % or less, or 1 wt. % or less) (e.g., as determined by XRPD, melting point. DSC. SSNMR, or polarized light microscopy). In some embodiments, the plurality of discrete particles is entirely free of crystalline psilocybin (e.g., as determined by XRPD, melting point, DSC, SSNMR, or polarized light microscopy).

In some instances, the amorphous (e.g., a-polymorphic) psilocybin (e.g., psilocybin component) comprises an amount of crystalline psilocybin that is at most 10 wt. % (e.g., 10 wt. % or less. 8 wt. % or less. 6 wt. % or less. 4 wt. % or less. 2 wt. % or less, or 1 wt. % or less) (e.g., as determined by XRPD, melting point. DSC. SSNMR, or polarized light microscopy). In some embodiments, the amorphous (e.g., a-polymorphic) psilocybin (e.g., psilocybin component) is entirely free of crystalline psilocybin (e.g., as determined by XRPD, melting point. DSC. SSNMR, or polarized light microscopy). In some embodiments, entirely free means undetectable (e.g., as determined by XRPD, melting point. DSC. SSNMR, or polarized light microscopy). In some instances, the amorphous (e.g., a-polymorphic) psilocybin composition is entirely free of crystalline psilocybin is an a-polymorphic psilocybin composition.

In some embodiments, in any of the compositions provided herein, the amorphous (e.g., a-polymorphic) psilocybin is at least 10% amorphous (e.g., at least 20% amorphous, at least 25% amorphous, at least 40% amorphous, at at least 50% amorphous, least 60% amorphous, at least 75% amorphous, at least 80% amorphous, at least 90% amorphous, at least 95% amorphous, at least 96% amorphous, at least 97% amorphous, at least 98% amorphous, at least 99% amorphous) (e.g., as measured by XRPD). In some embodiments, in any of the compositions provided herein, the amorphous (e.g., a-polymorphic) psilocybin is at least 60% amorphous. In some embodiments, in any of the compositions provided herein, the amorphous (e.g., a-polymorphic) psilocybin is at most 99.5% amorphous (e.g., at most 95% amorphous, at most 90% amorphous, at most 80% amorphous, at most 70% amorphous, at most 60% amorphous, at most 50% amorphous) (e.g., as measured by XRPD). In some embodiments, in any of the compositions provided herein, the amorphous (e.g., a-polymorphic) psilocybin is about 10% to about 99.5% amorphous, such as measured by XRPD.

In some embodiments, the psilocybin (e.g., psilocybin component (e.g., amorphous or a-polymorphic psilocybin)) has a (e.g., chemical and/or physical) purity (e.g., indicative of the amount of impurities (e.g., substances other than psilocybin) found in a sample) of at least 85 wt. %, at least 90 wt. %, at least 95 wt %, at least 96 wt. %, at least 97 wt. %, at least 98 wt. %, at least 99 wt. %, or at least 99.5 wt. %, and all values therebetween. In some embodiments, the psilocybin (e.g., synthetic, a-polymorphic psilocybin) has a (e.g., chemical and/or physical) purity of at least 95 wt. %. In some embodiments, the psilocybin (e.g., synthetic, a-polymorphic psilocybin) has a (e.g., chemical and/or physical) purity of at least 97 wt. %. In some embodiments, the psilocybin (e.g., synthetic, a-polymorphic psilocybin) has a (e.g., chemical and/or physical) purity of at least 98 wt. %. In some embodiments, the psilocybin (e.g., synthetic, a-polymorphic psilocybin) has a (e.g., chemical and/or physical) purity of at most 99.5 wt. %, at most 99 wt. %, at most 98 wt. %, at most 97 wt. %. In some embodiments, the psilocybin (e.g., synthetic, a-polymorphic psilocybin) has a (e.g., chemical and/or physical) purity of at most 99 wt. %. In some embodiments, the (e.g., chemical and/or physical) purity of a particle (e.g., one or more particle) of the plurality of discrete particles is at least 95 wt %, at least 96 wt. %, at least 97 wt. %, at least 98 wt. %, at least 99 wt. %, or at least 99.5 wt. %, and all values therebetween. In some instances, chemical purity is determined by titration, spectroscopy (e.g, infrared. UV-VIS), chromatography (e.g., HPLC TLC (Thin Layer Chromatography) or paper chromatography), optical rotation, mass spectrometry, or a combination thereof). In some instances, chemical purity is calculated as an average (e.g., as the average chemical purity of a sample of particles from a plurality of discrete particles). In some embodiments, physical purity is determined by melting point. XRPD. DSC (e.g., modulated DSC). SSNMR, or polarized light microscopy.

In some embodiments, the psilocybin (e.g., psilocybin component (e.g., amorphous or a-polymorphic psilocybin)) has a chemical purity (e.g., indicative of the amount of impurities (e.g., substances other than psilocybin) found in a sample) of at least 95 wt %, at least 96 wt. %, at least 97 wt. %, at least 98 wt. %, at least 99 wt. %, or at least 99.5 wt. %, and all values therebetween (e.g, as determined by, e.g. High Performance Liquid Chromatography (HPLC) or reverse-phase HPLC). In some embodiments, the psilocybin (e.g., synthetic, a-polymorphic psilocybin) has a chemical purity of at least 95 wt. %. In some embodiments, the psilocybin (e.g., synthetic, a-polymorphic psilocybin) has a chemical purity of at least 97 wt. %. In some embodiments, the psilocybin (e.g., synthetic, a-polymorphic psilocybin) has a chemical purity of at least 98 wt. %. In some embodiments, the psilocybin (e.g., synthetic, a-polymorphic psilocybin) has a chemical purity of at most 99.5 wt. %, at most 99 wt. %, at most 98 wt. %, at most 97 wt. %. In some embodiments, the psilocybin (e.g., synthetic, a-polymorphic psilocybin) has a chemical purity of at most 99 wt. %. In some embodiments, the chemical purity of a particle (e.g., one or more particle) of the plurality of discrete particles is at least 95 wt %, at least 96 wt. %, at least 97 wt. %, at least 98 wt. %, at least 99 wt. %, or at least 99.5 wt. %, and all values therebetween (e.g, as determined by, e.g. HPLC). In some instances, chemical purity is determined by titration, spectroscopy (e.g, infrared. UV-VIS), chromatography (e.g., HPLC TLC (Thin Layer Chromatography) or paper chromatography), optical rotation, mass spectrometry, or a combination thereof). In some instances, chemical purity is calculated as an average (e.g., as the average chemical purity of a sample of particles from a plurality of discrete particles).

In any of the compositions provided herein, in some embodiments, the psilocybin component comprises at most one impurity, at most two impurities, or at most three impurities. In some embodiments, the psilocybin component comprises at most one impurity, at most two impurities, at most three impurities, at most four impurities, at most five impurities, at most six impurities, at most seven impurities, at most eight impurities, at most nine impurities, at most ten impurities, at most eleven impurities, or at most twelve impurities. In some embodiments, the psilocybin component comprises at least one impurity, at least two impurities, or at least three impurities. In some embodiments, the psilocybin component comprises at least one impurity, at least two impurities, at least three impurities, at least four impurities, at least five impurities, at least six impurities, at least seven impurities, at least eight impurities, at least nine impurities, at least ten impurities, at least eleven impurities, or at least twelve impurities. In some embodiments, no single impurity (e.g., in the psilocybin) is present in a proportion greater than 2% (e.g., less than 2%, less than 1.5%, less than 1%, less than 0.5%, or less than 0.15%). In some embodiments, no single impurity (e.g., in the (e.g., a-polymorphic) psilocybin) is present in a proportion greater than 2%. In some embodiments, no single impurity (e.g., in the (e.g., a-polymorphic) psilocybin) is present in a proportion greater than 1%.

In some embodiments, any one of the compositions provided herein is carrier-free. In some embodiments, any one of the compositions provided herein is free of polymers. In some embodiments, the (e.g., amorphous (e.g., a-polymorphic)) psilocybin compositions provided herein are carrier-free. In some embodiments, the (e.g., amorphous (e.g., a-polymorphic)) psilocybin compositions provided herein are free of polymers. In some embodiments, the amorphous (e.g., a-polymorphic) compositions provided herein are free of polymers. In some embodiments, the amorphous (e.g., a-polymorphic) compositions provided herein are carrier-free.

In some embodiments, in any one of the compositions provided herein, the composition (e.g., (e.g., synthetic) a-polymorphic composition or amorphous psilocybin composition) comprises a polymer in an amount of less than 20% (e.g., less than 40%, less than 30%, less than 10%, less than 5%, less than 2.5%, less than 1%). In some embodiments, the composition (e.g., (e.g., synthetic) a-polymorphic composition or amorphous psilocybin composition) comprises a polymer in an amount of less than 5%. In some embodiments, the composition (e.g., (e.g., synthetic) a-polymorphic composition or amorphous psilocybin composition) comprises a polymer in an amount of at least 0.1% (e.g., at least 1%, at least 5%, at least 10%, at least 20%). In some embodiments, the composition (e.g., (e.g., synthetic) a-polymorphic composition or amorphous psilocybin composition) comprises a polymer in an amount of about 0.1% to about 30%.

In some embodiments, any one of the compositions provided herein is not a dispersion (e.g. solid). In some embodiments, any one of the compositions does not comprise psilocybin (e.g., a-polymorphic psilocybin or amorphous psilocybin) dispersed throughout a solid, such as a polymeric matrix.

In some embodiments, the composition comprises a carrier (e.g., a carrier component). In some embodiments, the plurality of discrete particles comprises a carrier (e.g., a carrier component). In some instances, the carrier (e.g., the carrier component) is an excipient. In some instances, the carrier component comprises one carrier. In some embodiments, the carrier component comprises one or more carriers. In some instances, the carrier component comprises two, three, four or five carriers.

In some embodiments, the carrier comprises a polymer. In some embodiments, the carrier comprises a polymer carrier. In some embodiments, the polymer (carrier) comprises (e.g., at least a portion of) acacia gelatin, colloidal silicon dioxide, calcium glycerophosphate, calcium lactate, maltodextrin, glycerin, magnesium silicate, polyvinylpyrrolidone (PVP), polyvinyl pyrrolidone-co-vinyl acetate, polyacrylic acid (PAA), polyvinyl alcohol (PVA), cholesterol, cholesterol esters, sodium caseinate, soy lecithin, taurocholic acid, phosphotidylcholine, sodium chloride, tricalcium phosphate, dipotassium phosphate, cellulose (e.g., a cellulose conjugate or microcrystalline cellulose), sugars, sodium stearoyl lactylate, carrageenan, monoglyceride, diglyceride, polyethylene glycol (PEG), poly(ethylene glyco-propylene glycol-ethylene glycol)triblock copolymers, hydroxypropyl methylcellulose (HPMC), hydroxypropyl methylcellulose acetate succinate (HPMCAS), porous calcium silicate, magnesium aluminum metasilicate, and pregelatinized starch, a portion thereof, or combinations thereof.

In some embodiments, the carrier (e.g., the polymer (carrier)) is selected from the group consisting of acacia, gelatin, colloidal silicon dioxide, calcium glycerophosphate, calcium lactate, maltodextrin, glycerin, magnesium silicate, polyvinylpyrrolidone (PVP), polyvinyl pyrrolidone-co-vinyl acetate, polyacrylic acid (PAA), polyvinyl alcohol (PVA), cholesterol, cholesterol esters, sodium caseinate, soy lecithin, taurocholic acid, phosphotidylcholine, sodium chloride, tricalcium phosphate, dipotassium phosphate, cellulose (e.g., a cellulose conjugate or microcrystalline cellulose), sugars, sodium stearoyl lactylate, carrageenan, monoglyceride, diglyceride, polyethylene glycol (PEG), poly (ethylene glyco-propylene glycol-ethylene glycol) triblock copolymers, hydroxypropyl methylcellulose (HPMC), hydroxypropyl methylcellulose acetate succinate (HPMCAS), porous calcium silicate, magnesium aluminum metasilicate, and pregelatinized starch, or at least a portion thereof, or combinations thereof.

In some embodiments, any one of the compositions provided herein may comprise a sugar, such as any suitable sugar. In some embodiments, any one of the compositions provided herein may comprise mannitol, trehalose, sucrose, glucose, dextrose, molasses, and lactose. In some embodiments, the composition comprises mannitol. In some embodiments, the composition comprises trehalose. In some embodiments, the composition comprises sucrose. In some embodiments, the composition comprises glucose. In some embodiments, the composition comprises sucrose. In some embodiments, the composition comprises dextrose. In some embodiments, the composition comprises sucrose. In some embodiments, the composition comprises molasses. In some embodiments, the composition comprises sucrose. In some embodiments, the composition comprises lactose. In some instances, the psilocybin (e.g., a-polymorphic or amorphous psilocybin) is not present in a matrix of the sugar. In some instances, the sugar assists with long term stability of the compositions provided herein. In some instances, the sugar assists with product handling, such as flowability, such as in spray drying of a composition provided herein. In some instances, the sugar assists with product handling, such as reconstitution of the lyophilisate, such as in lyophilisation of a composition provided herein.

In some embodiments, any one of the compositions provided herein may comprise silicon dioxide. In some embodiments, the silicon dioxide assists with product handling, such as flowability, such as in spray drying of a composition provided herein.

In some embodiments, at least a portion of the psilocybin (e.g., the psilocybin component) comprises amorphous (e.g., a-polymorphic) psilocybin (e.g., weight % or volume %) as determined by XRPD. DSC (e.g., modulated DSC). SSNMR, polarized light microscopy, spectroscopy, melting point, or solution calorimetry.

In some embodiments, the composition (e.g., the amorphous (e.g., a-polymorphic) psilocybin composition) comprises 1 wt. % to 100 wt. % (e.g., at least 40 wt. %, at least 50 wt. %, at least 60 wt. %, at least 70 wt. %, at least 80 wt. % at least 90 wt. %, at least 99 wt. %, or more) psilocybin (e.g., amorphous (e.g., a-polymorphic) psilocybin (e.g., the amorphous psilocybin component)). In some embodiments, the composition (e.g., the amorphous (e.g., a-polymorphic) psilocybin composition) has a wt. % of psilocybin (e.g., the amorphous (e.g., a-polymorphic) psilocybin (e.g., the amorphous psilocybin component)) that is 40 wt. % or more. 50 wt. % or more. 60 wt. % or more. 70 wt. % or more. 80 wt. % or more. 90 wt. % or more. 99 wt. % or more. In some embodiment, the composition (e.g., the amorphous (e.g., a-polymorphic) psilocybin composition) has a wt. % of psilocybin (e.g., the amorphous (e.g., a-polymorphic) psilocybin (e.g., the amorphous psilocybin component)) that is 99 wt. % or less. 90 wt. % or less. 80 wt. % or less. 70 wt. % or less. 60 wt. % or less. 50 wt. % or less. 40 wt. % or less. In some embodiment, the composition (e.g., the amorphous (e.g., a-polymorphic) psilocybin composition) has a wt. % of psilocybin (e.g., the amorphous psilocybin (e.g., the amorphous psilocybin component)) that is at least 80 wt. %, at least 85 wt. %, at least 90 wt. %, at least 95 wt. %, or more.

In some embodiments, the plurality of discrete particles comprises 1 wt. % to 100 wt. % (e.g., at least 40 wt. %, at least 50 wt. %, at least 60 wt. %, at least 70 wt. %, at least 80 wt. % at least 90 wt. %, at least 99 wt. %, or more) psilocybin (e.g., amorphous (e.g., a-polymorphic) psilocybin (e.g., the amorphous psilocybin component)). In some embodiments, the plurality of discrete particles has a wt. % of psilocybin (e.g., the amorphous (e.g., a-polymorphic) psilocybin (e.g., the amorphous psilocybin component)) that is 40 wt. % or more. 50 wt. % or more. 60 wt. % or more. 70 wt. % or more. 80 wt. % or more. 90 wt. % or more. 99 wt. % or more. In some embodiment, the plurality of discrete particles has a wt. % of psilocybin (e.g., the amorphous (e.g., a-polymorphic) psilocybin (e.g., the amorphous psilocybin component)) that is 99 wt. % or less. 90 wt. % or less. 80 wt. % or less. 70 wt. % or less. 60 wt. % or less. 50 wt. % or less. 40 wt. % or less. In some embodiment, the plurality of discrete particles has a wt. % of psilocybin (e.g., the amorphous (e.g., a-polymorphic) psilocybin (e.g., the amorphous psilocybin component)) that is at least 80 wt. %, at least 85 wt. %, at least 90 wt. %, at least 95 wt. %, or more.

In some embodiments, the psilocybin component (e.g., as described herein) comprises 1 wt. % to 100 wt. % (e.g., at least 40 wt. %, at least 50 wt. %, at least 60 wt. %, at least 70 wt. %, at least 80 wt. % at least 90 wt. %, at least 99 wt. %, or more) psilocybin (e.g., amorphous (e.g., a-polymorphic) psilocybin (e.g., the amorphous psilocybin component)). In some embodiments, the psilocybin component (e.g., as described herein) has a wt. % of psilocybin (e.g., amorphous (e.g., a-polymorphic) psilocybin) that is 40 wt. % or more. 50 wt. % or more. 60 wt. % or more. 70 wt. % or more. 80 wt. % or more. 90 wt. % or more. 99 wt. % or more. In some embodiments, the psilocybin component (e.g., as described herein) has a wt. % of psilocybin (e.g., amorphous (e.g., a-polymorphic) psilocybin) that is 99 wt. % or less, 90 wt. % or less, 80 wt. % or less, 70 wt. % or less, 60 wt. % or less, 50 wt. % or less, 40 wt. % or less. In some embodiments, the psilocybin component (e.g., as described herein) has a wt. % of psilocybin (e.g., amorphous (e.g., a-polymorphic) psilocybin) that is at least 80 wt. %, at least 85 wt. %, at least 90 wt. %, at least 95 wt. %, or more.

In some embodiments, the composition (e.g., the amorphous (e.g., a-polymorphic) psilocybin composition) has 1 wt. % to 100 wt. % (e.g., at most 1 wt. %, at most 10 wt. %, at most 20 wt. %, at most 30 wt. %, at most 40 wt. % at most 50 wt. %, at most 60 wt. %, or less) of a carrier (e.g., the carrier component, such as, comprising a carrier (e.g., excipient) provided herein)). In some embodiments, the composition (e.g., the amorphous (e.g., a-polymorphic) psilocybin composition) has a wt. % of carrier (e.g., such as, an carrier (e.g., excipient) provided herein)) that is 1 wt. % or less, 10 wt. % or less, 20 wt. % or less, 30 wt. % or less, 40 wt. % or less, 50 wt. % or less, 60 wt. % or less. In some embodiments, the composition (e.g., the amorphous (e.g., a-polymorphic) psilocybin composition) has a wt. % of carrier (e.g., the carrier component, such as, comprising a carrier (e.g., excipient) provided herein)) that is 60 wt. % or more, 50 wt. % or more, 40) wt. % or more, 30 wt. % or more, 20 wt. % or more, 10 wt. % or more, 1 wt. % or more. In some embodiment, the composition (e.g., the amorphous (e.g., a-polymorphic) psilocybin composition) has a wt. % of carrier (e.g., the carrier component, such as, comprising a carrier (e.g., excipient) provided herein)) that is most 20 wt. %, at most 15 wt. %, at most 10 wt. %, at most 5 wt. %, or less.

In some embodiments, the plurality of discrete particles has 1 wt. % to 100 wt. % (e.g., at most 1 wt. %, at most 10 wt. %, at most 20 wt. %, at most 30 wt. %, at most 40 wt. % at most 50 wt. %, at most 60 wt. %, or less) of a carrier (e.g., the carrier component, such as, comprising a carrier (e.g., excipient) provided herein)). In some embodiments, the plurality of discrete particles has a wt. % of carrier (e.g., such as, an carrier (e.g., excipient) provided herein)) that is 1 wt. % or less. 10 wt. % or less, 20 wt. % or less, 30 wt. % or less, 40 wt. % or less, 50 wt. % or less, 60 wt. % or less. In some embodiment, the plurality of discrete particles has a wt. % of carrier (e.g., the carrier component, such as, comprising a carrier (e.g., excipient) provided herein)) that is 60 wt. % or more, 50 wt. % or more, 40 wt. % or more, 30 wt. % or more, 20 wt. % or more, 10 wt. % or more, 1 wt. % or more. In some embodiment, the plurality of discrete particles has a wt. % of carrier (e.g., the carrier component, such as, comprising a carrier (e.g., excipient) provided herein)) that is most 20 wt. %, at most 15 wt. %, at most 10 wt. %, at most 5 wt. %, or less.

In some embodiments, the composition (e.g., the amorphous (e.g., a-polymorphic) psilocybin composition) has a ratio of carrier (e.g., the carrier component) to psilocybin (e.g., psilocybin component (e.g., amorphous (e.g., a-polymorphic) psilocybin)) that is 1:99 to about 99:1, about 1:99 to about 90:10, about 25:75 to about 75:25, about 40:60 to about 60:40, or about 80:20 to about 50:50. In some embodiments, the composition (e.g., the amorphous (e.g., a-polymorphic) psilocybin composition) has a ratio of carrier (e.g., the carrier component) to psilocybin (e.g., psilocybin component (e.g., amorphous (e.g., a-polymorphic) psilocybin)) that is about 1:99, about 5:95, about 10:90, about 15:85, or about 20:80.

In some embodiments, the plurality of discrete particles (e.g., the amorphous (e.g., a-polymorphic) psilocybin composition) has a ratio of carrier (e.g., the carrier component) to psilocybin (e.g., psilocybin component (e.g., amorphous (e.g., a-polymorphic) psilocybin)). In some embodiments, one or more discrete particle of plurality of discrete particles (e.g., the amorphous (e.g., a-polymorphic) psilocybin composition) has a ratio of carrier (e.g., the carrier component) to psilocybin (e.g., psilocybin component (e.g., amorphous (e.g., a-polymorphic) psilocybin)). In some embodiments, each particle of plurality of discrete particles (e.g., the amorphous (e.g., a-polymorphic) psilocybin composition) has a ratio of carrier (e.g., the carrier component) to psilocybin (e.g., psilocybin component (e.g., amorphous (e.g., a-polymorphic) psilocybin)). In some embodiments, the ratio of carrier to psilocybin is about 1:99 to about 99:1, about 1:99 to about 90:10, about 25:75 to about 75:25, about 40:60 to about 60:40, or about 80:20 to about 50:50. In some embodiments, the composition (e.g., the amorphous (e.g., a-polymorphic) psilocybin composition) has a ratio of carrier (e.g., the carrier component) to psilocybin (e.g., psilocybin component (e.g., amorphous (e.g., a-polymorphic) psilocybin)) that is about 1:99, about 5:95, about 10:90, about 15:85, or about 20:80. In some instances, the ratio of carrier to psilocybin is an average ratio (e.g., an average ratio calculated using each of the plurality of discrete particles.

In some instances, an amorphous solid has better pharmacokinetic and/or pharmacokinetic characteristics (e.g., solubility) than a crystalline solid. In some instances, amorphous (e.g., a-polymorphic) psilocybin has better pharmacokinetic and/or pharmacokinetic characteristics (e.g., solubility, bioavailability, or the like) than crystalline psilocybin. In some instances, amorphous (e.g., a-polymorphic) psilocybin is useful in providing a low dose of psilocybin (e.g., to an individual in need thereof). In some instances, an amorphous solid dispersion (ASD) increases the stability of an amorphous compound. In some instances, an ASD is an amorphous composition of an active agent and a polymer. In some instances, the pH of the amorphous (e.g, a-polymorphic) psilocybin increases the stability of the amorphous composition. In some instances, the purity of the amorphous (e.g, a-polymorphic) psilocybin increases the stability of the amorphous composition.

In some embodiments, a composition provided herein (e.g., an amorphous (e.g., a-polymorphic) psilocybin composition) comprises an amorphous solid dispersion (ASD). In some embodiments, a composition provided herein (e.g., an amorphous (e.g., a-polymorphic) psilocybin composition) is an ASD.

In some embodiments, a discrete particle (e.g., one or more discrete particle) of a plurality of discrete particles comprises an ASD. In some embodiments, at least one discrete particle of the plurality of discrete particles comprises an ASD. In some embodiments, a plurality of discrete particles (e.g., as provided herein) comprises an ASD. In some embodiments, a plurality of discrete particles (e.g., as provided herein) is an ASD.

Provided herein, in some embodiments, is a plurality of discrete particles, comprising a carrier component comprising at least one carrier; and a psilocybin component comprising amorphous (e.g., a-polymorphic) psilocybin (e.g., as determined by XRPD, DSC, melting point, SSNMR, or polarized light microscopy). In some embodiments, the composition comprises one or more discrete particle of the plurality of discrete particles. In some embodiments, the composition comprises a plurality of discrete particles. In some embodiments, each of the plurality of discrete particles comprises at least a portion of the carrier component. In some embodiments, one or more of the plurality of discrete particles comprises at least a portion of the carrier component. In some embodiments, each of the plurality of discrete particles comprises at least a portion of the psilocybin component. In some embodiments, one or more of the plurality of discrete particles comprises at least a portion of the psilocybin component. In some embodiments, each of the plurality of discrete particles independently comprises at least a portion of the carrier component. In some embodiments, each of the plurality of discrete particles independently comprises at least a portion of the psilocybin component. In some embodiments, each of the plurality of discrete particles independently comprises at least a portion of the carrier component and at least a portion of the psilocybin component.

In some embodiments, the at least one discrete particle of the plurality of discrete particles comprises at least one discrete domain embedded in a matrix. In some embodiments, each of the at least one discrete particle of the plurality of discrete particles comprises at least one discrete domain embedded in a matrix.

In some embodiments, the at least one discrete particle of the plurality of discrete particles comprises at least one discrete domain (e.g., comprising at least a portion of the psilocybin component and/or at least a portion of the carrier component). In some embodiments, each of the discrete particles of the plurality of discrete particles comprises at least one discrete domain (e.g., comprising at least a portion of the psilocybin component and/or at least a portion of the carrier component). In some embodiments, the discrete particle (e.g., comprising a discrete domain) comprises a portion of amorphous (e.g., a-polymorphic) psilocybin (e.g., the psilocybin component). In some embodiments, the discrete particle (e.g., comprising a discrete domain) comprises a portion of a carrier (e.g., the carrier component). In some embodiments, the discrete particle (e.g., comprising a discrete domain) comprises a portion of the psilocybin component and a portion of the carrier component. In some embodiments, the discrete particle (e.g., comprising a discrete domain) comprises an additional agent (e.g., as provided elsewhere herein).

In some embodiments, the at least one discrete particle of the plurality of discrete particles comprises a plurality of discrete domains (e.g., each discrete domain independently comprising at least a portion of amorphous (e.g., a-polymorphic) psilocybin (e.g., the psilocybin component) and/or a carrier (e.g., the carrier component)). In some embodiments, each discrete domain independently comprises at least a portion of the psilocybin component. In some embodiments, each discrete domain independently comprises at least a portion of the carrier component. In some embodiments, each discrete domain independently comprises at least a portion of the psilocybin component and at least a portion of the carrier component.

In some embodiments, the at least one discrete particle of the plurality of discrete particles comprises a matrix (e.g., comprising at least a portion of the psilocybin component and/or the carrier component). In some embodiments, each of the discrete particles of the plurality of discrete particles comprises a matrix (e.g., comprising at least a portion of the psilocybin component and/or at least a portion of the carrier component). In some embodiments, the matrix (e.g., comprising at least one discrete domain) comprises a portion of amorphous (e.g., a-polymorphic) psilocybin (e.g., the psilocybin component). In some embodiments, the matrix (e.g., comprising at least one discrete domain) comprises a portion of a carrier (e.g., the carrier component). In some embodiments, the matrix (e.g., comprising at least one discrete domain) comprises a portion of the psilocybin component and a portion of the carrier component. In some embodiments, the matrix (e.g., comprising at least one discrete domain) comprises an additional agent (e.g., as provided elsewhere herein).

In some embodiments, the at least one discrete particle of the plurality of discrete particles comprises a plurality of matrixes (e.g., each matrix independently comprising at least a portion of amorphous (e.g., a-polymorphic) psilocybin (e.g., the psilocybin component) and/or a portion of the carrier (e.g., the carrier component)). In some embodiments, each matrix independently comprises at least a portion of the psilocybin component. In some embodiments, each matrix independently comprises at least a portion of the carrier component. In some embodiments, each matrix independently comprises at least a portion of the psilocybin component and the carrier component.

In some embodiments, the matrix comprises a portion of the carrier component and the discrete domain comprises a portion of the psilocybin component (e.g., amorphous (e.g., a-polymorphic) psilocybin).

In some embodiments, the matrix comprises a portion of the psilocybin component and the discrete domain comprises a portion of the carrier component.

In some embodiments, the at least one discrete particle of the plurality of discrete particles comprises a matrix. In some embodiments, the matrix comprises the carrier component. In some embodiments, the matrix comprises a portion of the carrier component. In some embodiments, the matrix comprises the psilocybin component. In some embodiments, the matrix comprises a portion of the psilocybin component. In some embodiments, the matrix comprises the carrier component and the psilocybin component. In some embodiments, the matrix comprises a portion of the carrier component and a portion of the psilocybin component. In some embodiments, the matrix comprises an additional agent. In some embodiments, the matrix comprises a portion of the additional agent.

In some embodiments, the at least one discrete particle of the plurality of discrete particles comprises a discrete domain and a matrix. In some embodiments, a discrete particle of the plurality of discrete particles comprises a discrete domain embedded in a matrix. In some embodiments, each discrete particle of the plurality of discrete particles comprises a discrete domain and a matrix. In some embodiments, at discrete particle of the plurality of discrete particles comprises a discrete domain outside of a matrix. In some embodiments, the discrete particle comprises a matrix within a discrete domain. In some embodiments, the discrete particle comprises a discrete domain mixed with a matrix.

In some embodiments, the matrix comprises psilocybin ((e.g., psilocybin component) e.g., amorphous (e.g., a-polymorphic) psilocybin)) and the discrete domain comprises the carrier (e.g., carrier component). In some embodiments, the matrix comprises a portion of the psilocybin and the discrete domain comprises a portion of the carrier. In some embodiments, the matrix comprises the carrier and the discrete domain comprises the psilocybin. In some embodiments, the matrix comprises a portion of the carrier and the discrete domain comprises a portion of the psilocybin.

In some embodiments, the ASD comprises an amorphous solid solution or semi-solid solution. In some instances, the amorphous solid solution or semi-solid solution comprises a carrier (e.g., a carrier component (e.g., amorphous carrier component)) mixed with psilocybin (e.g., amorphous (e.g., a-polymorphic) psilocybin (e.g., a psilocybin component)).

In some embodiments, the ASD comprises psilocybin (e.g., amorphous (e.g., a-polymorphic) psilocybin) in a psilocybin rich phase and a carrier ((e.g., carrier component) e.g., amorphous carrier component)) in a carrier rich phase (e.g., dispersion). In some embodiments, the dispersion is a solid or semi-solid dispersion.

In some embodiments, the at least one (e.g., one or more) discrete particle of the plurality of discrete particles comprises a heterogenous mixture of components (e.g., each component being in one or more (e.g., two) different phases (e.g., a dispersion (e.g., solid or semi-solid)).

In some embodiments, the at least one (e.g., one or more) discrete particle of the plurality of discrete particles comprises a solid dispersion of psilocybin (e.g, psilocybin component) in a carrier component. In some embodiments, the at least one discrete particle of the plurality of discrete particles comprises a semi-solid dispersion of psilocybin in a carrier component.

In some instances, the dispersion is a solid dispersion. In some embodiments, the dispersion is a semi-solid dispersion. The dispersion (e.g., solid or semi-solid) may be a dispersion of one or more active ingredient (e.g., psilocybin) in a carrier (e.g., carrier component). In some embodiments, the dispersion (e.g., solid or semi-solid) comprises psilocybin ((e.g., a psilocybin component (e.g., amorphous (e.g., a-polymorphic) psilocybin)). In some embodiments, the dispersion (e.g., solid or semi-solid) comprises a carrier component. In some embodiments, the dispersion (e.g., solid or semi-solid) comprises psilocybin in a carrier component. In some embodiments, the dispersion (e.g., solid or semi-solid) comprises a carrier (e.g., carrier component) in psilocybin (e.g., psilocybin component). In some embodiments, the solid dispersion is a powder (e.g., a loose powder and/or a compressed powder).

In some embodiments, a semi-solid dispersion is selected from the group consisting of a gel (e.g., hydrogel), an ointment, a cream, a lotion, an emulsion (e.g., microemulsion), and a paste.

In some instances, the dispersion is a liquid dispersion. The liquid dispersion may be a dispersion of one or more active ingredient (e.g., psilocybin) in a carrier (e.g., carrier component). In some embodiments, the liquid dispersion comprises psilocybin (e.g., amorphous (e.g., a-polymorphic) psilocybin (e.g., a psilocybin component). In some embodiments, the liquid dispersion comprises a carrier component. In some embodiments, the liquid dispersion comprises psilocybin in a carrier component. In some embodiments, the liquid dispersion comprises a carrier (e.g., carrier component) in psilocybin (e.g., psilocybin component). In some embodiments, the liquid dispersion is selected from the group consisting of a solution, a dispersion, a suspension and an emulsion.

In some embodiments, the at least one (e.g., one or more) discrete particle of the plurality of discrete particles comprises a mixture containing two or more substances in the same phase (e.g., a solution (e.g., solid or semi-solid solution)).

In some embodiments, the at least one (e.g., one or more) discrete particle of the plurality of discrete particles comprises a solid solution of psilocybin in a carrier component. In some embodiments, the at least one discrete particle of the plurality of discrete particles comprises a semi-solid solution of psilocybin in a carrier component.

The solution (e.g., solid or semi-solid) may be a solution of one or more active ingredient (e.g., psilocybin) in a carrier (e.g., carrier component). In some embodiments, the solution (e.g., solid or semi-solid) comprises psilocybin ((e.g., a psilocybin component (e.g., amorphous (e.g., a-polymorphic) psilocybin)). In some embodiments, the solution (e.g., solid or semi-solid) comprises a carrier component. In some embodiments, the solution (e.g., solid or semi-solid) comprises psilocybin in a carrier component. In some embodiments, the solution (e.g., solid or semi-solid) comprises a carrier (e.g., carrier component) in psilocybin (e.g., psilocybin component). In some embodiments, the solid solution is a powder (e.g., a loose powder and/or a compressed powder). In some embodiments, a semi-solid solution is selected from the group consisting of a gel (e.g., hydrogel), an ointment, a cream, a lotion, an emulsion (e.g., microemulsion), and a paste.

In some instances, the solution is a liquid solution. The liquid solution may be a solution of one or more active ingredient (e.g., psilocybin) in a carrier (e.g., carrier component). In some embodiments, the liquid solution comprises psilocybin ((e.g., a psilocybin component (e.g., amorphous (e.g., a-polymorphic) psilocybin)). In some embodiments, the liquid solution comprises a carrier component. In some embodiments, the liquid solution comprises psilocybin in a carrier component. In some embodiments, the liquid solution comprises a carrier (e.g., carrier component) in psilocybin (e.g., psilocybin component).

In some embodiments, the composition comprises an agent. In some embodiments, the plurality of discrete particles comprises an agent. In some embodiments, the agent comprises a carrier (e.g., a carrier component). In some embodiments, the agent comprises an additional agent. In some embodiments, the agent comprises an additional agent and a carrier. In some embodiments, the discrete plurality of particles is within the agent. In some embodiments, the agent is within the discrete plurality of particles. In some embodiments, the discrete plurality of particles is adjacent to the agent.

In some embodiments, the composition comprises one or more active agent. In some embodiments, each particle of the plurality of discrete particles comprises one or more active agents. In some embodiments, one or more particle of the plurality of discrete particles comprises one or more active agents. In some embodiments, the one or more active agent is psilocybin (e.g., amorphous (e.g., a-polymorphic) psilocybin (e.g., the psilocybin component)). In some embodiments, the one or more active agent is an additional agent. In some embodiments, the composition comprises an additional agent. In some embodiments, the at least one discrete particle of the plurality of discrete particles comprises an additional agent. In some embodiments, each discrete particle of the plurality of discrete particles comprises an additional agent. In some embodiments, the matrix comprises and additional agent. In some embodiments, the discrete domain comprises an additional agent.

In some embodiments, the additional agent is a 5HT receptor agonist (e.g, other than psilocybin), stimulant, an antihistamine, an antiemetic, an antidepressant, an anti-inflammatory, a growth factor, a lithium compound, resveratrol, phosphatidylcholine, curcumin, magnesium. melatonin, pregnenolone, ginseng, tryptophan, lysergic acid diethylamide, a 5HT receptor antagonist, an anxiolytic or a mood stabilizer, and combinations thereof.

In some embodiments, the one or more (i.e., at least one) discrete particle of the plurality of discrete particles has a ratio of the carrier component to the psilocybin component (e.g., amorphous (e.g., a-polymorphic) psilocybin) that is about 1:99 to about 99:1 (e.g., on average), about 1:99 to about 90:10 (e.g., on average), about 25:75 to about 75:25 (e.g., on average), about 40:60 to about 60:40 (e.g., on average), or about 80:20 to about 50:50 (e.g., on average). In some embodiments, the one or more (i.e., at least one) discrete particle of the plurality of discrete particles has a ratio of carrier (e.g., the carrier component) to psilocybin (e.g., psilocybin component (e.g., amorphous (e.g., a-polymorphic) psilocybin)) that is about 1:99 (e.g., on average), about 5:95 (e.g., on average), about 10:90 (e.g., on average), about 15:85 (e.g., on average), or about 20:80 (e.g., on average).

In some embodiments, each discrete particle of the plurality of discrete particles has a ratio of the carrier component to the psilocybin component (e.g., amorphous (e.g., a-polymorphic) psilocybin) that is about 1:99 to about 99:1 (e.g., on average), about 1:99 to about 90:10 (e.g., on average), about 25:75 to about 75:25 (e.g., on average), about 40:60 to about 60:40 (e.g., on average), or about 80:20 to about 50:50 (e.g., on average). In some embodiments, each discrete particle of the plurality of discrete particles has a ratio of carrier (e.g., the carrier component) to psilocybin (e.g., psilocybin component (e.g., amorphous (e.g., a-polymorphic) psilocybin)) that is about 1:99 (e.g., on average), about 5:95 (e.g., on average), about 10:90 (e.g., on average), about 15:85 (e.g., on average), or about 20:80 (e.g., on average).

Any particle provided herein may be of any suitable size (e.g., large or small), and may be prepared by any of the methods provided herein (e.g., hot melt extrusion, spray-drying, wet/granulation and fluid, microwave or tray drying, freeze-drying, drum-drying, precipitating (e.g., crash precipitating), supercritical fluidization, or the like).

In some embodiments, the content of the composition, such as, for example, the at least a portion of the carrier component and/or the at least a portion of the psilocybin component (in the composition), is determined by a method (e.g., provided herein) for characterizing the (e.g., structural) order of a (e.g., pharmaceutical) composition, such as, provided elsewhere herein. In some embodiments, the content (e.g., amount, ratio, wt %, or the like) of psilocybin (component) (e.g., the amorphous (e.g., a-polymorphic) psilocybin) of the composition is determined using a method (e.g., such as, provided herein) for characterizing the order (e.g., structural) of a composition (e.g., pharmaceutical), such as, provided elsewhere herein. In some instances, a portion of the psilocybin component and/or the carrier component comprises psilocybin (e.g., amorphous (e.g., a-polymorphic) psilocybin).

In some embodiments, the content (e.g., amount, ratio, wt %, or the like) of the at least a portion of the carrier component and/or the at least a portion of the psilocybin component in the composition is determined by X-ray powder diffraction (XRPD), differential scanning calorimetry (DSC) (e.g., modulated DSC), solid-state nuclear magnetic resonance (SSNMR), melting point, polarized light microscopy, or any combination thereof. In some embodiments, the structural order and/or disorder of the psilocybin (e.g., amorphous) component is determined by XRPD, DSC, SSNMR, melting point, or polarized light microscopy, or any combination thereof.

In some instances, the (e.g., amount, ratio, wt %, or the like) portion of the carrier component and/or the portion of the psilocybin component in the composition is determined by a spectroscopy method (e.g., Raman, infrared, or near-infrared).

In some embodiments, the composition is a pharmaceutical composition. In some embodiments, the composition is a pharmaceutical composition (e.g., a composition used to treat (e.g., heal or cure) or alleviate (e.g., reduce or make less severe) a symptom (e.g., physical or mental), biomarker, or other manifestation (e.g., sign (e.g., diagnostic, pathognomic, prognostic, or anamnestic)) associated with an illness or disorder, or an illness or disorder.

In some embodiments, the pharmaceutical composition is suitable for (e.g., oral) administration to an individual (e.g., a rodent, a monkey, a human, etc. (e.g., in need thereof)).

In some embodiments, the pharmaceutical composition is suitable for enteral (e.g., oral, rectal, or the like) administration. In some embodiments, the pharmaceutical composition is suitable for oral administration. Suitable forms of pharmaceutical compositions for oral administration include tablets, capsules, orally designating formulations (e.g., tablets and films), sublingual medications, buccal medications, oral liquid, ocular, vaginal, formulations, or combinations thereof.

In some embodiments, the composition is prepared using any suitable technique (e.g., for forming an amorphous composition and/or an ASD). In some instances, the technique produces an amorphous composition (e.g., an amorphous solid dispersion or amorphous (e.g., a-polymorphic) psilocybin). In some embodiments, the technique produces an amorphous plurality of discrete particles. In some embodiments, the technique comprises spray-drying (e.g., a spray-dried composition and/or spray-dried particles), hot-melt extruding (e.g., a hot-melt extrusion composition and/or hot-melt extrusion particles), freeze-drying (e.g., a freeze-dried composition and/or freeze-dried particles), melt quenching (e.g., a melt quenched composition and/or melt quenched particles), ball milling (e.g., a ball milled composition and/or ball milled particles), cryogrinding (e.g., a cryoground composition and/or cryoground particles), desolvating (e.g., a desolvated composition and/or desolvated particles), precipitating (e.g., a precipitated composition and/or precipitated particles), drum drying (e.g., a drum dried composition and/or drum-dried particles), pulse combustion drying (e.g., a pulse combustion dried composition and/or pulse combustion dried particles), crash precipitating (e.g., a crash precipitation composition and/or crash precipitation particles), supercritical fluidizing (e.g., a supercritical fluidization composition and/or supercritical fluidization particles), wet granulation followed by particle drying (e.g, fluid bed, microwave or tray drying), or a combination thereof.

In some embodiments, the composition is selected from the group consisting of a spray-dried composition, a freeze-dried composition, a drum-dried composition, a hot-melt extrusion composition, a precipitation composition (e.g, crash precipitation), a super critical fluidization composition, a wet granulated dried composition and a pulse combustion dried composition.

In some embodiments, the composition is a spray-dried composition (e.g., produced by rapidly drying a liquid or slurry with a hot gas or emulsification/solvent removal).

In some embodiments, the composition is a hot-melt extrusion composition (e.g., produced by applying heat and pressure to a polymer to melt the polymer and then forcing the polymer through an orifice).

In some embodiments, the composition is a spray-dried composition or a hot-melt extrusion composition.

In some embodiments, the composition is a drum dried composition (e.g., produced by rotating components of the composition in drums, over a temperature, in order to dry liquids in the components).

In some embodiments, the composition is a crash precipitation composition (e.g., produced by separating solid particles from a liquid (e.g., a precipitation composition)).

In some embodiments, the composition is a supercritical fluidized composition (e.g., produced by fluidizing the composition with supercritical fluids (e.g., any substance at a temperature and pressure above its critical point, but below the pressure required to compress the substance into a solid) with a supercritical fluidized bed).

In some embodiments, the composition is a pulse combustion dried composition (e.g., produced by utilizing one or more pulse combustors to produce high temperature and high-velocity pulsating jects to dry components of the composition).

In some embodiments, any one of the compositions (e.g., (e.g., synthetic) a-polymorphic composition or amorphous psilocybin composition) provided herein is stable for any suitable period of time. "Stability" as used herein may refer to chemical or physical stability.

In some embodiments, any one of the compositions (e.g., (e.g., synthetic) a-polymorphic composition or amorphous psilocybin composition) provided herein is chemically stable for any suitable period of time. In some embodiments, the composition (e.g., (e.g., synthetic) a-polymorphic composition or amorphous psilocybin composition) is chemically stable for at least 1 week (e.g., at least 2 weeks, at least 1 month, at least 2 months, at least 3 months, at least 4 months, at least 6 months), such as at ambient conditions. In some embodiments, the composition (e.g., (e.g., synthetic) a-polymorphic composition or amorphous psilocybin composition) is chemically stable for at least 1 month, such as at ambient conditions. In some embodiments, the composition (e.g., (e.g., synthetic) a-polymorphic composition or amorphous psilocybin composition) is chemically stable for at most 1 year (e.g., at most 6 months, at most 4 months, at most 2 months, at most 1 month), such as at ambient conditions. In some embodiments, the composition (e.g., (e.g., synthetic) a-polymorphic composition or amorphous psilocybin composition) is chemically stable for about 1 week to about 1 year, such as at ambient conditions. In some embodiments, the chemical stability may refer to at least 99.5% (e.g., at least 99%, at least 98%, at least 97%, at least 95%, at least 90%) of psilocybin remaining (e.g., did not degrade) after a period of time. In some embodiments, at least 95% of psilocybin remains (e.g., did not degrade) after 1 month, such as at ambient conditions.

Figure 3:
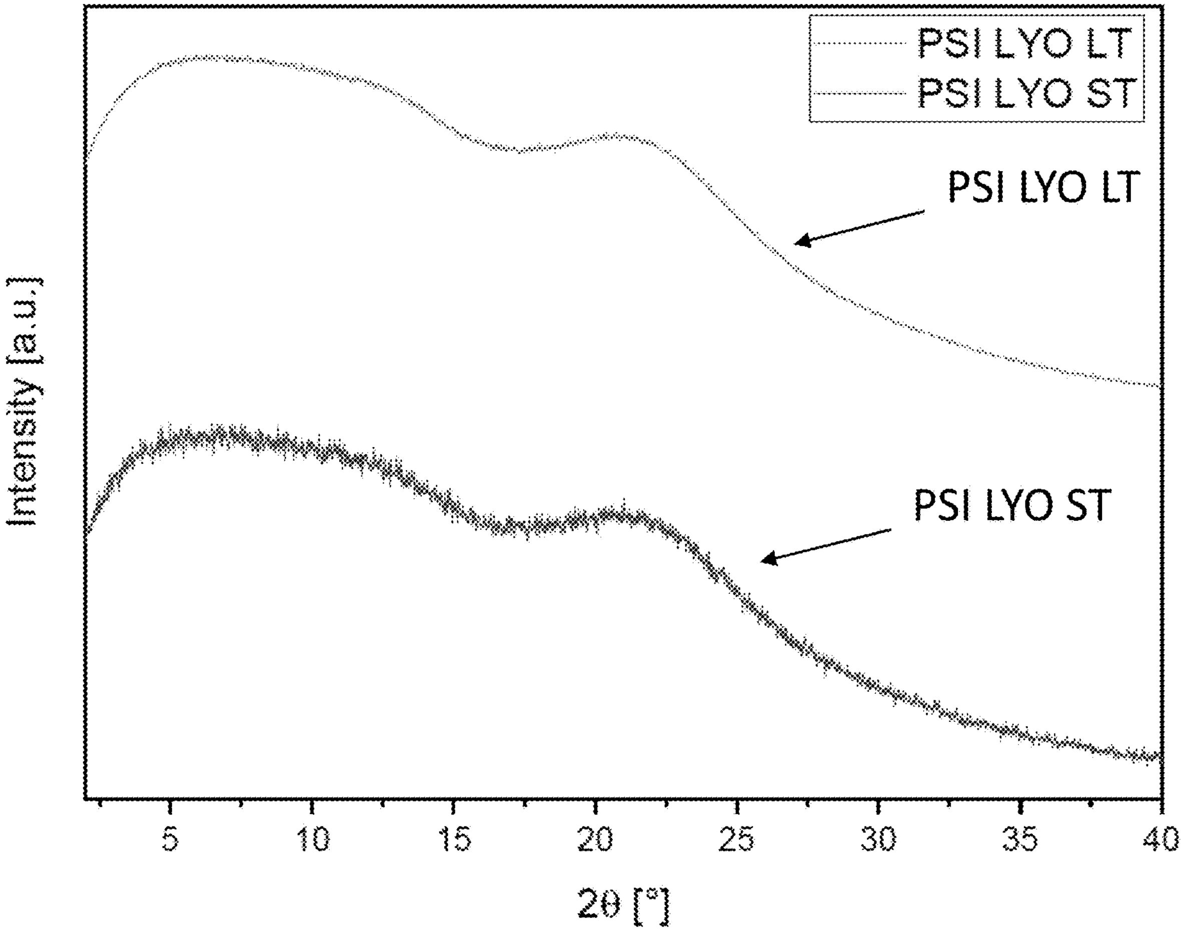
FIG. 3 illustrates XRPD of lyophilized psilocybin (short scan) (PSI LYO ST) and lyophilized psilocybin (long scan) (PSI LYO LT) following 1 week at room temperature.

Psilocybin has a tendency to crystallize when prepared in its amorphous form. In some embodiments, any one of the compositions provided herein (e.g., (e.g., synthetic) a-polymorphic composition or amorphous psilocybin composition) is physically stable for any suitable amount of time. In some embodiments, the composition (e.g., (e.g., synthetic) a-polymorphic composition or amorphous psilocybin composition) is physically stable for at least 1 week (e.g., at least 2 weeks, at least 1 month, at least 2 months, at least 3 months, at least 4 months, at least 6 months), such as at ambient conditions. In some embodiments, the composition (e.g., (e.g., synthetic) a-polymorphic composition or amorphous psilocybin composition) is physically stable for at most 1 year (e.g., at most 6 months, at most 4 months, at most 2 months, at most 1 month, at most 2 weeks). In some embodiments, the composition (e.g., (e.g., synthetic) a-polymorphic composition or amorphous psilocybin composition) is physically stable for about 1 week to about 1 year, such as at ambient conditions. In some embodiments, the composition (e.g., (e.g., synthetic) a-polymorphic composition or amorphous psilocybin composition) is stable for at least 1 month, such as at ambient conditions. Physical stability may refer to lack of phase transitions, such as an amorphous to a crystalline phase transition or lack of hydration of the solid. In some embodiments, the physical stability can be assessed by XRPD as described in Example 3 (FIG. 3). In other embodiments, the physical stability can be determined by melting point. DSC (e.g., modulated DSC). SSNMR, or polarized light microscopy. In some embodiments, the physical stability is assessed by melting point. In some embodiments, the physical stability is assessed by DSC (e.g., modulated DSC). In some embodiments, the physical stability is assessed by SSNMR. In some embodiments, the physical stability is assessed by polarized light microscopy, for example, as described in Example 3.

In some embodiments, any one of the compositions provided herein (e.g., (e.g., synthetic) a-polymorphic composition or amorphous psilocybin composition) is carrier free (e.g., free of polymers) and is entirely free of crystalline psilocybin for at least 1 week (e.g., at least 2 weeks, at least 1 month, at least 2 months, at least 4 months, at least 6 months). In some embodiments, any one of the compositions provided herein (e.g., (e.g., synthetic) a-polymorphic composition or amorphous psilocybin composition) is carrier free (e.g., free of polymers) and is entirely free of crystalline psilocybin after at most 1 year (e.g., at most 6 months, at most 4 months, at most 2 months, at most 1 month). In some embodiments, the composition (e.g., (e.g., synthetic) a-polymorphic composition or amorphous psilocybin composition) is carrier free (e.g., free of polymers) and is entirely free of crystalline psilocybin after about 1 week to about 1 year. In some embodiments, the composition provided herein (e.g., (e.g., synthetic) a-polymorphic composition or amorphous psilocybin composition) is carrier free (e.g., free of polymers) and is entirely free of psilocybin for at least 4 weeks, such as described in Example 3. In some embodiments, the compositions are entirely free of crystalline psilocybin after any suitable period of time (e.g., of storage) at room temperature. In other embodiments, the compositions are entirely free of crystalline psilocybin after any suitable period of time (e.g., of storage) at decreased temperatures. In some embodiments, the compositions are entirely free of crystalline psilocybin after any suitable period of time (e.g., of storage) at elevated temperatures.

In some embodiments, any one of the compositions provided herein (e.g., (e.g., synthetic) a-polymorphic composition or amorphous psilocybin composition) is carrier free (e.g., free of polymers) and is substantially free of crystalline psilocybin for at least 1 week (e.g., at least 2 weeks, at least 1 month, at least 2 months, at least 4 months, at least 6 months). In some embodiments, any one of the compositions provided herein (e.g., (e.g., synthetic) a-polymorphic composition or amorphous psilocybin composition) is carrier free (e.g., free of polymers) and is substantially free of crystalline psilocybin after at most 1 year (e.g., at most 6 months, at most 4 months, at most 2 months, at most 1 month). In some embodiments, the composition (e.g., (e.g., synthetic) a-polymorphic composition or amorphous psilocybin composition) is carrier free (e.g., free of polymers) and is substantially free of crystalline psilocybin after about 1 week to about 1 year. In some embodiments, the composition provided herein (e.g., (e.g., synthetic) a-polymorphic composition or amorphous psilocybin composition) is carrier free (e.g., free of polymers) and is substantially free of psilocybin for at least 4 weeks, such as described in Example 3. In some embodiments, the compositions are substantially free of crystalline psilocybin after any suitable period of time (e.g., of storage) at room temperature. In other embodiments, the compositions are substantially free of crystalline psilocybin after any suitable period of time (e.g., of storage) at decreased temperatures. In some embodiments, the compositions are substantially free of crystalline psilocybin after any suitable period of time (e.g., of storage) at elevated temperatures.

In some embodiments is provide a synthetic, a-polymorphic psilocybin that is entirely free of crystalline psilocybin (e.g., as determined by XRPD, melting point. DSC (e.g, modulated DSC). SSNMR, or polarized light microscopy) (e.g. XRPD scan is free of reflexes or peaks). In some embodiments, the synthetic, a-polymorphic psilocybin has a chemical purity of at least 95% (e.g, at least 95%, 96%, 97%, 98%, 99% or 99.5% and all values therebetween), as determined by, e.g. High Performance Liquid Chromatography (HPLC) or Reverse-Phase HPLC, with no single impurity greater that 2% (e.g, less than 2%, less than 1%, less than 0.5%, less than 0.15%). In some embodiments, the synthetic, a-polymorphic psilocybin has a chemical purity of at least 98%. In some embodiments, the synthetic, a-polymorphic psilocybin is concentrated. In some embodiments, the synthetic, a-polymorphic psilocybin is a spray-dried a-polymorphic psilocybin. In some embodiments, the synthetic, a-polymorphic psilocybin is a lyophilized a-polymorphic psilocybin.

Manufacturing Amorphous Psilocybin

Provided herein, in some embodiments, are methods for producing any one of the compositions provided herein. Provided herein, in some embodiments, are methods for producing any amorphous psilocybin (e.g., psilocybin component) provided herein. Provided herein, in some embodiments, are methods for producing any a-polymorphic psilocybin composition provided herein. In some embodiments, the method for producing amorphous (e.g., a-polymorphic) psilocybin comprises (i) providing (e.g., synthesizing) a psilocybin component: (ii) combining the psilocybin component with a carrier component, the carrier component comprising at least one carrier to produce a psilocybin-carrier composition; and (iii) processing the psilocybin-carrier composition to produce (e.g., an amorphous composition comprising) one or more particles comprising the amorphous (e.g., a-polymorphic) psilocybin (e.g., component) and the carrier component. In some embodiments, providing psilocybin (e.g., psilocybin component) comprises synthesizing psilocybin (e.g., amorphous (e.g., a-polymorphic) psilocybin). In some instances, providing psilocybin (e.g., psilocybin component) comprises synthesizing psilocybin (e.g., amorphous (e.g., a-polymorphic) psilocybin) without producing a crystalline (e.g, psilocybin) intermediary (an a-polymorphic psilocybin). In some embodiments, without producing a crystalline (e.g, psilocybin) intermediary means avoiding producing psilocybin in crystalline form.

In some embodiments, combining (e.g., mixing, folding, layering, or the like) the psilocybin (e.g., psilocybin component (e.g., amorphous (e.g., a-polymorphic) psilocybin)) with a carrier (e.g., carrier component) produces a psilocybin-carrier composition (e.g., any of the compositions described herein).

In some embodiments, processing the psilocybin-carrier composition produces (e.g., a composition (e.g., amorphous composition) comprising one or more particles comprising psilocybin (e.g., psilocybin component (e.g., amorphous (e.g., a-polymorphic) psilocybin)) and the carrier (e.g., carrier component (e.g., comprising at least one carrier)).

In some embodiments, the psilocybin component comprises psilocybin. In some embodiments, the psilocybin component comprises amorphous (e.g., a-polymorphic) psilocybin.

Provided herein, in some embodiments, are methods for producing an amorphous composition comprising psilocybin (e.g., amorphous (e.g., a-polymorphic) psilocybin). In some embodiments, the method for producing an amorphous composition comprising psilocybin comprises a.) synthesizing a psilocybin component; and b.) producing an amorphous composition comprising the psilocybin component. In some instances, synthesizing a psilocybin component comprises synthesizing psilocybin (e.g., amorphous (e.g., a-polymorphic) psilocybin) without producing a crystalline (e.g, psilocybin) intermediary. In some embodiments, the producing an amorphous composition is lyophilization.

In some embodiments, the method for producing amorphous (e.g., a-polymorphic) psilocybin comprises processing the psilocybin-carrier composition to produce amorphous (e.g., a-polymorphic) psilocybin (e.g., an ASD). In some embodiments, the method for producing one or more particles comprises processing (e.g., the psilocybin (e.g., psilocybin component) and/or the carrier (e.g., carrier component)).

In some embodiments, the psilocybin component is the only component of the amorphous composition.

In some embodiments, processing (e.g., producing) is selected from the group consisting of spray drying, freeze drying, drum drying, precipitating (e.g., crash precipitation), hot-melt extrusion, super critical fluidization and pulse combination drying or a combination thereof. In some embodiments, processing is selected from the group consisting of spray drying, wet granulation/fluid drying, wet granulation/microwave drying, wet granulation/tray drying, freeze drying (e.g., lyophilization), drum drying, precipitating (e.g., crash precipitation), hot-melt extrusion, super critical fluidization and pulse combination drying or a combination thereof.

In some embodiments, provided herein is a method of making any one of the compositions provided herein. In some embodiments, provided herein is a method of making any one of the synthetic, a-polymorphic psilocybin provided herein. In some embodiments, provided herein is an amorphous (e.g., a-polymorphic) psilocybin composition provided herein. In some embodiments, provided herein is a method of making a synthetic, a-polymorphic psilocybin composition. In some embodiments, provided herein is a method of making any one of the psilocybin provided herein. In some embodiments, provided herein is an amorphous (e.g., a-polymorphic) psilocybin provided herein. In some embodiments, provided herein is a method of making a synthetic, a-polymorphic psilocybin.

In some embodiments, at least 50% (e.g., at least 60%, at least 70%, at least 80%, at least 90%, at least 95%, at least 97%, at least 99%, at least 99.5%) of the composition is comprised of the amorphous (e.g., a-polymorphic) psilocybin. In some embodiments, at most 99.5% (e.g., at most 99%, at most 97%, at most 95%, at most 80%, at most 70%) of the composition is comprised of the amorphous (e.g., a-polymorphic) psilocybin. In some embodiments about 50% to about 99.5% of the composition is comprised of the amorphous (e.g., a-polymorphic) psilocybin.

In some embodiments, the method includes synthesis of Benzyl {3-12-(Benzyldimethylammonio)ethyl]-1H-indol-4-yl} Phosphate according to Schemes 1-3 of Example 2 and synthesis of amorphous (e.g., a-polymorphic) psilocybin according to Scheme 4 of Example 2. In some embodiments, the method includes synthesis of protected psilocybin (e.g. Benzyl {3-[2-(Benzyldimethylammonio)ethyl]-1H-indol-4-yl} Phosphate) according to any known methods of the prior art (e.g. Sherwood et al. Synthesis 2020. 52. 688-694: Hofmann. A, et al. Helv. Chim. Acta 1959, 42, 1557; Nichols. D. E.; Frescas. S. Synthesis, 1999, 935; Kargbo et al. ACS Omega 2020, 5. 16959-16966) and synthesis of amorphous (e.g., a-polymorphic) psilocybin according to Scheme 4 of Example 2. In some embodiments, the method comprises a liquid-liquid extraction to purify the the amorphous (e.g., a-polymorphic) psilocybin. In some instances, the pH of the liquid-liquid extraction increases the purity of the amorphous (e.g., a-polymorphic) psilocybin. In some instances, the pH of the liquid-liquid extraction increases the stability of the amorphous (e.g., a-polymorphic) psilocybin. In some instances, the purity of the amorphous (e.g., a-polymorphic) psilocybin increases the stability of the amorphous composition.

In one embodiment, there is provided a method of making a synthetic, a-polymorphic psilocybin, the method comprising:

a. providing Benzyl {3-|2-(Benzyldimethylammonio) ethyl]-1H-indol-4-yl} Phosphate;
b. deprotecting the Benzyl {3-[2-(Benzyldimethylammonio)ethyl|-1H-indol-4-yl} Phosphate in a reaction solvent to provide psilocybin:
c. extracting the psilocybin from the reaction solvent into an aqueous medium and washing the aqueous medium with an organic solvent:
d. concentrating the aqueous medium comprising the psilocybin; and
e. collecting the amorphous (e.g, a-polymorphic) psilocybin.

In some embodiments, the method comprises providing a protected psilocybin. In some embodiments, the protected psilocybin is represented by the structure:

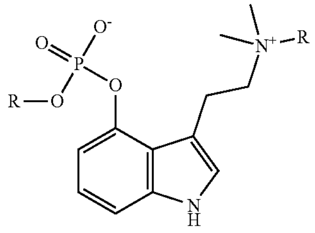

In some embodiments, each R is independently hydrogen or a protecting group. In some embodiments, both R are hydrogen. In some embodiments, both R are protecting group. In some embodiments, one R is a hydrogen and one R is a protecting group. In some embodiments, the protecting groups comprise benzene. In some embodiments, the protecting groups comprise methylbenzene.

In some embodiments, the synthesis of the protected psilocybin is described in Example 2. In some instances, the synthesis of protected psilocybin comprises the synthesis of 6 (3-[2-(dimethylamino) 2-oxoacetyl]-1H-indol-4-yl acetate from 1H-indol-4-yl acetate followed by synthesis of psilocin and subsequently the synthesis of the protected psilocybin, such as described in Example 2 and Schemes 1-3.

In some embodiments, the method comprises deprotecting the protected psilocybin. In some embodiments, the method comprises deprotecting the protected psilocybin in a reaction solvent. In some embodiments, the reaction solvent comprises an alcohol. In some embodiments, the alcohol may comprise any suitable alcohol according to one skilled in the art. In some embodiments, the alcohol comprises methanol, ethanol, tert-butanol, butanol, pentanol, or hexanol. In some embodiments, the alcohol comprises methanol. In some embodiments, the deprotecting comprises hydrogenolysis.

In some embodiments, the method comprises extracting the psilocybin from the reaction solvent. In some embodiments, the method comprises extracting the psilocybin into an aqueous medium. In some embodiments, the method comprises extracting the psilocybin from the reaction solvent into an aqueous medium. In some embodiments, the method comprises washing the aqueous medium with an organic solvent. In some embodiments, the method comprises extracting the psilocybin from the reaction solvent into an aqueous medium and washing the aqueous medium with an organic solvent. In some embodiments, the reaction solvent may be dissolved in the aqueous medium. In some embodiments, the reaction solvent may be immiscible with the aqueous medium. In some embodiments, the reaction solvent may be exposed to the aqueous medium before it is exposed to the organic solvent.

In some embodiments, in any of the methods provided herein, the organic solvent comprises any suitable organic solvent to extract the psilocybin. In some embodiments, the organic solvent comprises a halocarbon. In some embodiments, the organic solvent comprises dichloromethane.

In some embodiments, in any of the methods provided herein, the aqueous medium has a pH of about 8 to about 10. In some embodiments, in any of the methods provided herein, the aqueous medium has a pH of about 7 to about 11. In some embodiments, in any of the methods provided herein, the aqueous medium has a pH of about 9. In some embodiments, in any of the methods provided herein, the aqueous medium has a pH of about 8.5. In some embodiments, in any of the methods provided herein, the aqueous medium has a pH of about 9.5. In some embodiments, in any of the methods provided herein, the aqueous medium has a pH of about 8. In some embodiments, in any of the methods provided herein, the aqueous medium has a pH of about 10. In some embodiments, the selection of the pH may improve the extraction of the psilocybin into the aqueous layer. In some embodiments, the pH of about 9 may be critical to extraction of the psilocybin into the aqueous layer.

In some embodiments, the methods provided herein comprise concentration the aqueous medium. In some embodiments, the methods provided herein comprise partially concentrating the aqueous medium. In some embodiments, the methods provided herein comprise completely concentrating the aqueous medium. In some embodiments, concentrating comprises spray drying, such as spray drying provided elsewhere herein, some embodiments, concentrating comprises spray drying, such as described in Example 3. In some embodiments, concentrating comprises lyophilization, such as lyophilization provided elsewhere herein. In some embodiments, concentrating comprises lyophilization, such as described in Example 3. In some instances, the psilocybin product of concentrating is stable for at least 1 week, such as described in Example 3.

In some embodiments, the methods provided herein comprise collecting the amorphous solid, such as after concentrating the aqueous medium.

In some embodiments, during no point in any of the methods provided herein, is the psilocybin in a crystalline state.

In some embodiments, the methods provided herein (e.g., producing) comprise lyophilization. In some embodiments, concentration comprises lyophilizing. In some embodiments, lyophilization is conducted in the absence of a carrier material. In some embodiments, lyophilization is conducted in the absence of a polymer. In some embodiments, the absence of a polymer comprises lyophilizing the amorphous (e.g., a-polymorphic) psilocybin with no carrier (e.g., polymer). In some embodiments, the absence of a polymer comprises lyophilizing the amorphous (e.g., a-polymorphic) psilocybin with less than 10%, 9%. 8%, 7%, 6%, 5%. 4%. 3%. 2%, or 1% of a carrier (e.g., polymer). In some embodiments, lyophilization is conducted in the presence of one or more sugars, such as sugars described elsewhere herein. In some embodiments, the sugars comprise mannitol and/or trehalose. In some embodiments, the sugars comprise mannitol. In some embodiments, the sugars comprise trehalose. In some embodiments, when lyophilization is conducted in the presence of a sugar, the ratio of psilocybin to sugar is about 90:10 to about 10:90, such as described in Example 3. In some embodiments, the ratio of psilocybin to sugar is 50:50. In some embodiments, the ratio of psilocybin to sugar is 25:75. In some embodiments, the ratio of psilocybin to sugar is 75:25.

In some embodiments, lyophilization provided herein comprises a starting temperature of about room temperature. In some embodiments, lyophilization provided herein comprises cooling the temperature of the condenser to less than −20° C. (e.g., less than −30° C., less than −40° C., less than −50° C., less than −60° C.). In some embodiments, lyophilization provided herein comprises cooling the temperature of the condenser to more than −90° C. (e.g., more than −80° C., more than −70° C., more than −60° C., more than −50° C.). In some embodiments, lyophilization comprises cooling to about −20° C., to about −90° C. In some embodiments, lyophilization provided herein comprises cooling the temperature of the condenser to about −54° C.

In some embodiments, lyophilization provided herein comprises a pressure in the lyophilizer of at least 0.0001 mbar (e.g., at least 0.001 mbar, at least 0.01 mbar). In some embodiments, the lyophilization provided herein comprises a pressure in the lyophilizer of at most 0.1 mbar (e.g., at most 0.01 mbar, at most 0.001 mbar). In some embodiments, lyophilization provided herein comprises a pressure in the lyophilizer of about 0.0001 mbar to about 0.1 mbar. In some embodiments lyophilization provided herein comprises a pressure in the lyophilizer of about 0.01 mbar.

In some embodiments, lyophilization provided herein is completed for at least 12 hours (e.g., at least 16 hours, at least 24 hours, at least 36 hours, at least 48 hours). In some embodiments, lyophilization provided herein is completed for at most 72 hours (e.g., at most 48 hours, at most 36 hours, at most 24 hours). In some embodiments, lyophilization provided herein is completed for about 12 hours to about 72 hours. In some embodiments, lyophilization provided herein is completed for 24 hours.

In some embodiments, the mass of the lyophilized solution is at least 0.1 g (e.g., at least 1 g, at least 2 g, at least 4 g, at least 6 g, at least 8 g). In some embodiments, the mass of the lyophilized solution is at most 10 g (e.g., at most 8 g, at most 6 g, at most 4 g, at most 2 g, at most 1 g). In some embodiments, the mass of the lyophilized solution is about 0.1 g to about 10 g. In some embodiments, the mass of the lyophilized solution is about 5.81 g. 8.29 g. 7.11 g. 4.06 g. 6.22 g, or 1.45 g.

In some embodiments, the mass of the product provided by lyophilization herein is at least 5 mg (e.g., at least 10 mg, at least 30 mg, at least 50 mg, at least 70 mg). In some embodiments. the mass of the product provided by lyophilization herein is at most 100 mg (e.g., at most 90 mg, at most 80 mg, at most 70 mg, at most 60 mg, at most 50 mg). In some embodiments, the mass of the product provided by lyophilization herein is about 5 mg to about 100 mg. In some embodiments, mass of the product provided by lyophilization is 57.9 mg. 83.1 mg. 70.8 mg. 71.0 mg. 40.7 mg. 61.9 mg, or 14.4 mg.

In some embodiments, lyophilization provided herein results in an amorphous (e.g., a-polymorphic) psilocybin, such as described in Example 3 and FIG. 1. In some instances, the identity of the lyophilized material (e.g., amorphous (e.g., a-polymorphic) psilocybin) can be verified by proton NMR, as described in Example 3 and FIG. 2.

In some embodiments, the methods provided herein (e.g., producing) comprise spray drying. In some embodiments, concentrating comprises spray drying. In some embodiments, spray drying is conducted in the absence of a carrier material. In some embodiments, spray drying is conducted in the absence of a polymer. In some embodiments, the absence of a carrier comprises spray drying the amorphous (e.g., a-polymorphic) psilocybin with no carrier (e.g., polymer). In some embodiments, the absence of a polymer comprises spray drying the amorphous (e.g., a-polymorphic) psilocybin with less than 10%, 9%. 8%, 7%, 6%. 5%, 4%. 3%. 2%, or 1% of a carrier (e.g., polymer). In some embodiments, spray drying is conducted in the presence of one or more sugars, such as sugars described elsewhere herein. In some embodiments, the sugars comprise mannitol and/or trehalose. In some embodiments, the sugars comprise mannitol. In some embodiments, the sugars comprise trehalose. In some embodiments, spray drying is conducted in the presence of silicon dioxide. In some embodiments, the silicon dioxide or sugars assist with product handling, such as flowability, of the composition. In some embodiments, when spray drying is conducted in the presence of a sugar, the ratio of psilocybin to sugar is about 90:10 to about 10:90, such as described in Example 3. In some embodiments, the ratio of psilocybin to sugar is 50:50. In some embodiments, the ratio of psilocybin to sugar is 25:75. In some embodiments, the ratio of psilocybin to sugar is 75:25.

In some embodiments, spray drying provided herein is completed for at least 20 minutes (e.g., at least 30 minutes, at least 40 minutes, at least 50 minutes). In some embodiments, spray drying provided herein is completed for at most 60 minutes (e.g., at most 50 minutes, at most 40) minutes, at most 30 minutes). In some embodiments, spray drying provided herein is completed for about 20 minutes to about 60 minutes.

In some embodiments, in spray drying provided herein, the temperature of the drying gas at the inlet to the drying chamber is at least 90° C. (e.g., at least 95° C., at least 100° C., at least 105° C. at least 110° C.). In some embodiments, in spray drying provided herein, the temperature of the drying gas at the inlet to the drying chamber is at most 140° C. (e.g., at most 130°, at most 125° C. at most 120° C., at most 115° C., at most 110° C.). In some embodiments, in spray drying provided herein, the temperature of the drying gas at the inlet to the drying chamber is about 90° C., to about 140° C. In some embodiments, in spray drying provided herein, the temperature of the drying gas at the inlet to the drying chamber is about 110° C., in spray drying provided herein, the temperature of the drying gas at the inlet to the drying chamber is about 120° C.

In some embodiments, in spray drying provided herein, the frequency of the piezoelectric membrane (e.g., spray %) is at least 40% (e.g., at least 45%, at least 50%, at least 55%, at least 60%). In some embodiments, in spray drying provided herein, the frequency of the piezoelectric membrane (e.g., spray %) is at most 80% (e.g., at most 75%, at most 65%, at most 60%). In some embodiments, in spray drying provided herein, the frequency of the piezoelectric membrane (e.g., spray %) is about 40% to about 80%. In some embodiments, in spray drying provided herein, the frequency of the piezoelectric membrane (e.g., spray %) is about 60%.

In some embodiments, in spray drying provided herein, the pump rotation direction is clockwise with normal speed (e.g., pump rate 1). In some embodiments, in spray drying provided herein, the pump rotation is clockwise with double speed (e.g., pump rate 2).

In some embodiments, in spray drying provided herein, the cooling temperature is at least 0° C. (e.g., at least 1° C., at least 2° C., at least 3° C., at least 4° C., at least 6° C., at least 8° C.). In some embodiments, in spray drying provided herein, the cooling temperature is at most 15° C. (e.g., at most 13° C., at most 11° C., at most 9° C., at most 7°). In some embodiments, in spray drying provided herein, the cooling temperature is about 0)° C., to about 15° C. In some embodiments, the cooling temperature is about 6° C., about 7° C., or about 8° C.

In some embodiments, in spray drying provided herein, the mass of the solution being spray dried is at least 10 g (e.g., at least 15 g, at least 20 g, at least 25 g, at least 30 g, at least 35 g). In some embodiments, in spray drying provided herein, the mass of the solution being spray dried is at most 50 g (e.g., at most 45 g, at most 40 g, at most 35 g, at most 30 g, at most 25 g, at most 20 g). In some embodiments, in spray drying provided herein, the mass of the solution being spray dried is about 10 g to about 50 g. In some embodiments, the mass of the solution being spray dried is about 31.97 g, about 30.20 g, about 31.60 g, about 31.05 g, about 35.02 g, about 32.35 g, or about 17.05 g.

In some embodiments, in spray drying provided herein, the mass of the product is at least 0.005 g (e.g., at least 0.01 g, at least 0.05 g, at least 0.075 g, at least 0.1 g). In some embodiments, in spray drying provided herein, the mass of the product is at most 0.2 g (e.g., at most 0.175 g, at most 0.15 g, at most 0.125 g, at most 0.1 g). In some embodiments, the mass of the product is about 0.005 g to about 0.2 g. In some embodiments, the mass of the product is 0.13 g. 0.08 g. 0.14 g. 0.02 g, or 0.07 g.

In some embodiments, in any of the methods provided herein, the producing provides amorphous (e.g., a-polymorphic) psilocybin that is entirely free of crystalline psilocybin (e.g., as determined by XRPD, melting point. DSC. SSNMR, or polarized light microscopy) (e.g. XRPD scan is free of reflexes or peaks). In some embodiments, in any of the methods provided herein, the producing provides amorphous (e.g., a-polymorphic) psilocybin that is substantially free of crystalline psilocybin (e.g., as determined by XRPD, melting point. DSC. SSNMR, or polarized light microscopy).

In some embodiments, the method for producing amorphous (e.g., a-polymorphic) psilocybin produces a psilocybin component (e.g, a psilocybin component that is entirely free of crystalline psilocybin (e.g., as determined by XRPD, melting point. DSC. SSNMR, or polarized light microscopy) (e.g. XRPD scan is free of reflexes or peaks). In some embodiments, the method for producing amorphous (e.g., a-polymorphic) psilocybin produces a psilocybin component (e.g. a psilocybin component that is substantially free of crystalline psilocybin (e.g., as determined by XRPD, melting point. DSC (e.g., modulated DSC). SSNMR, or polarized light microscopy).

In some embodiments, the methods provided herein provide psilocybin (e.g., psilocybin component, amorphous (e.g., a-polymorphic) psilocybin, or a-polymorphic psilocybin) compositions that have a chemical purity described elsewhere herein, such as determined by HPLC or reverse-phase HPLC. In some embodiments, the methods provided herein provide psilocybin (e.g., psilocybin component, amorphous psilocybin, or a-polymorphic psilocybin) compositions that have a physical purity described elsewhere herein.

In some embodiments, the methods provided herein provide psilocybin (e.g., psilocybin component, amorphous psilocybin, or a-polymorphic psilocybin) compositions that have no single impurity greater than 2% (e.g., less than 2%, less than 1%, les than 0.5%, less than 0.15%). In some embodiments, the methods provided herein provide amorphous (e.g., a-polymorphic) psilocybin compositions that have no single impurity greater than 2% (e.g., less than 2%, less than 1%, less than 0.5%, less than 0.15%).

Method of Treatment

Provided herein, in some embodiments, are methods of administering any composition (e.g., amorphous (e.g., a-polymorphic) psilocybin, or a plurality of particles) provided herein to an individual (e.g., in need thereof).

In some embodiments, the method comprises administering the composition or plurality of particles (e.g., any of the compositions and/or plurality of discrete particles disclosed herein) to an individual (e.g., a rodent, a monkey, a human, etc. (e.g., in need thereof)). In some embodiments, the individual comprises a disorder or symptom. In some embodiments, administering the composition (e.g., a therapeutically effective amount) treats or manages an individual's disorder(s) or symptoms. An individual in need thereof may be suffering from a symptom or sign of a disorder. Administration of the composition may help prevent or decrease the progression of a disorder, decrease or prevent signs and/or symptoms of a disorder, and treat a disorder and/or a sign or symptom thereof. In some embodiments, the symptom is physical, behavioral, emotional, mental, or a combination thereof.

In some embodiments, the disorders, behavioral conditions, neuropsychiatric conditions, psychiatric conditions, and other conditions and symptoms thereof may be those specified in U.S. patent application Ser. No. 18/053,648, 18/102,268, 18/102,296, which are incorporated by reference herein in their entirety.

In some embodiments, the disorder is a symptom of a mental condition, a behavioral condition and/or a neuropsychiatric condition.

In some embodiments, the disorder is an attention condition (e.g., attention deficit disorder (ADD), attention-deficit hyperactivity disorder (ADHD), oppositional defiant disorder) or a cognitive (e.g., neurocognitive) condition. In some instances, the attention condition comprises inattention, hyperactivity, impulsivity, defiant behavior, drug use, criminal activity, or any combination thereof).

In some embodiments, the cognitive condition is a cognitive (e.g., mild or severe) impairment. In some embodiments, the cognitive condition (e.g., impairment) is dementia (e.g., with or without Lewy body presence. Creutzfeldt-Jakob disease, frontotemporal, Huntington's disease, Parkinson's disease dementia, vascular dementia, or a combination thereof). In some embodiments, the cognitive condition (e.g., impairment) is Alzheimer's disease (e.g., early-onset, late onset. Familial Alzheimer's). In some embodiments, the cognitive condition (e.g., impairment) is from a brain injury (e.g., traumatic brain injury, stroke, aneurysm, tumor, encephalitis, hydrocephalus, hypoxic and anoxic injuries, meningitis, and combinations thereof).

In some embodiments, the disorder is selected from the group consisting of schizophrenia, depression/suicide, anxiety, obsessive compulsive disorders (OCD), bipolar disorders, attention deficit hyperactivity disorder (ADHD), eating disorders such as anorexia nervosa, autism and autism spectrum disorders. Asperger's, neuropsychiatric diseases and disorders, sexual disorders such as erectile dysfunction, neurodegenerative diseases, inflammatory diseases, autoimmune diseases, metabolic diseases such as obesity and diabetes, central nervous system disorders, peripheral nervous system disorders. Alzheimer's disease, snoring, sleep apnea (obstructive sleep apnea, central sleep apnea), insomnia, sleep deprivation, restless legs syndrome, parasomnia, nightmares, night terrors, sleepwalking, hypersomnia (daytime sleepiness), narcolepsy, pain, and a combination thereof.

Further examples of the disorders, conditions and symptoms which may be managed or treated include by way of non-limiting example, apathy. Fragile λ syndrome. Down syndrome, migraine headache, cluster headache, psychiatric disorders, neurodevelopmental disorders, attention-deficit/hyperactivity disorder (ADHD), autism spectrum disorder, learning disorders, schizophrenia spectrum, psychotic disorders, bipolar disorders, depression, severe depression, major depressive disorder (MDD), premenstrual dysphoric disorder (PMDD), suicidality, mood related disorders, panic disorder, panic attack, phobias, agoraphobia, selective mutism, obsessive-compulsive disorder (OCD), hoarding disorder, hair-pulling disorder (trichotillomania), excoriation (skin-picking) disorder, substance-/medication-induced obsessive-compulsive disorder, trauma-related disorders, traumatic brain injury (TBI), post-traumatic stress disorder (PTSD), acute stress disorder, dissociative disorders, dissociative identity disorder, dissociative amnesia, anxiety, anxiety disorders, generalized anxiety disorder (GAD), social anxiety disorder, separation anxiety disorder, illness anxiety disorders, somatic disorders and diseases, somatic symptom disorder (hypochondriasis), factitious disorder, feeding disorders, eating disorders, anorexia, anorexia nervosa, bulimia nervosa, binge eating disorder, elimination disorders, enuresis, sleep disorders, insomnia, nightmare disorder, sleep apnea, central sleep apnea, narcolepsy, obstructive sleep apnea, hypopnea, and sleep-related hypoventilation, restless legs syndrome, jet lag, sexual dysfunction, premature ejaculation, erectile disorder, female orgasmic disorder, gender identity disorder, gender dysphoria, disruptive disorders, impulse-control disorders, conduct disorders, disruptive conduct disorders, impulse-control disorders, oppositional defiant disorder (ODD), aggression, kleptomania, pyromania, addictive disorders, substance dependence, substance abuse, alcoholism, drug addiction, opioid addiction, cocaine addiction, gambling addiction, tobacco dependence, food addiction, other forms of addiction to substances and behaviors, obesity, cognitive disorders, memory related disorders, learning related disorders, neurocognitive disorders. Alzheimer's disease, personality disorders, narcissistic personality disorders. Asperger syndrome. Tourette syndrome. Huntington's disease. Parkinson's disease. Lewy body disease, amyotrophic lateral sclerosis (ALS). Friedreich's ataxia, muscular atrophy, prion disease, dementia, vascular dementia, dementia/neurocognitive issues due to infection, dementia due to substance abuse or exposure to toxins, frontotemporal degeneration, mood disorders, delirium, aphasia, apraxia, agnosia, concussion, amnesia, anterograde amnesia, retrograde amnesia, body dysmorphic disorder, reactive attachment disorder, Fragile X syndrome. Down syndrome, migraines, migraine headache, cluster headache, cardiovascular disease, inflammatory conditions, fibromyalgia, pain, or a combination thereof.

In some embodiments, the disorder (e.g., mental, behavioral, or neuropsychiatric condition) is a Diagnostic and Statistical Manual of Mental Disorders (DSM-5) category. In some embodiments, the disorder (e.g., mental, behavioral, or neuropsychiatric condition) is a non-DSM-5 category (e.g., ICD-10) disorder. In some embodiments, the DSM-5 category disorder is induced by stress. In some embodiments, the non-DSM-5 category disorder is induced by stress. In some embodiments, the DSM-5 category disorder is induced by anxiety. In some embodiments, the non-DSM-5 category disorder is induced by anxiety. In some instances, anxiety is GAD, OCD, panic disorder. PTSD, instructive impulsivity, a phobia (e.g., social phobia (e.g., social anxiety disorder)), fear, or a combination thereof.

In some embodiments, the therapeutically effective amount of the composition comprises administering an amount of the composition that is below an adverse effect threshold (e.g., an amount insufficient to cause an adverse effect). In some embodiments, the adverse effect is selected from the group consisting of nausea, vomiting, hallucinations, panic attacks, psychosis, muscle weakness, a lack of coordination, or a combination thereof. In some instances, the adverse effect is a hallucination. Hallucinations are perturbations in the individual's sense of reality of perceptions, such as changes in perception, changes in physical function, or a combination thereof.

In some embodiments, the method comprises administering the composition (e.g., a plurality of discrete particles) to an individual. In some embodiments, administration is done enterally (e.g., orally, rectally, or the like).

In some embodiments, administrating the composition (e.g., a plurality of discrete particles) concurrently administering an additional agent. In some embodiments, administrating the composition (e.g., a plurality of discrete particles) comprises administering an additional agent before administering the composition. In some embodiments, administrating the composition (e.g., a plurality of discrete particles) comprises administering an additional agent after administering the composition.

In some embodiments, the composition (e.g., amorphous composition (e.g, comprising amorphous (e.g., a-polymorphic) psilocybin) is produced by any of the methods provided herein. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Amorphous psilocybin is prepared by crash precipitation using MTBE. A saturated solution of psilocybin (180 mg in 0.9 mL) is prepared in trifluoroethanol and an aliquot of this solution (0.45 mL) is filtered using a 0.45 μm PTFE filter directly into a vial containing 4.5 mL of methyl tert-butyl ether (MTBE) at ambient temperature. The suspension is centrifuged (3000 rpm for 3 mins), the solvent layer is removed and the remaining solid dried under a nitrogen stream overnight.

ASD Preparation

A 1% w/w PVP (polyvinylpyrrolidone) aqueous dispersion of 1 kg is prepared. 1 gram of amorphous Psilocybin solid is added to the aqueous dispersion with continuous mixing using propeller mixer. The dispersion is spray-dried to produce an amorphous solid dispersion.

Alternatively, a sufficient quantity of the saturated solution of Psilocybin solution in trifluoroethanol is added to the aqueous PVP dispersion to achieve a 10% drug load of the drug. The mixture is spray dried. The dispersion is spray-dried to produce an amorphous solid dispersion.

Example 2: Synthesis of Amorphous (e.g., a-polymorphic) Psilocybin Using Liquid-Liquid Extraction

Synthesis of Compound 6 (3-12-(dimethylamino) 2-oxoacetyl]-1H-indol-4-yl acetate A scheme of the synthesis of Compound 6 can be found in Scheme 1. A 2000 mL, four-necked, round-bottomed flask was equipped with an overhead stirrer, J-Kem temperature controller, a 250 mL dropping funnel, and rubber septum through which a positive pressure of dry $N_2$ was inserted. The septum was removed and the flask was charged sequentially with 1H-indol-4-yl acetate (5:50.1 g. 285 mmol, 1 equiv) and anhydrous Et20 (700 mL). The flask was resealed with the septum and is flushed with $N_2$. The suspension was stirred for 10 min and then cooled to (° C.) in an ice-water bath for 30 min. The dropping funnel was charged with a solution of oxalyl chloride (37.1 mL, 428 mmol, 1.5 equiv) in $Et_2O$ (60 mL). The oxalyl chloride solution was added dropwise at a rate sufficient to keep the temperature at or below 5° C., to minimize formation of dimer and other possible by-product. As the addition progressed, a yellow slurry of 10 was formed and when the addition was completed, the mixture was stirred for 4 h. The completion of the reaction was assaved by heating an aliquot of the reaction mixture in MeOH and checking by LCMS the conversion of compound 10 into the corresponding methyl ester [3-(2-methoxy-2-oxoacetyl]-1H-indol-4-yl acetate]. After this time, heptane (400 mL) was added and the mixture stirred for 30 min at 0° C.) The yellow solid obtained was quickly filtered and rinsed successively with heptane (2×300 mL), which was quickly used in the next step. Rinsing the solid with heptane removes excess oxalyl chloride, which prevents the formation of tetramethyloxalylamide in the formation of 6. Tetramethyloxalylamide becomes a detrimental impurity, which is difficult to remove in the synthesis of 6. Compound 10 was quickly dissolved in THF (500 mL) and cooled to 0° C. A 2.0 M solution of dimethylamine in THF (175 mL) was added dropwise at a rate sufficient to maintain temperature below 5° C., in order to minimize side reactions. After the addition was complete, pyridine (46 mL) in of THF (100 mL) was added dropwise and the mixture was stirred well for 60 min. Heptane (600 mL) was added and the flask contents were suction filtered via a Büchner funnel. The filtered residue was transferred into a roundbottomed flask and deionized H2O (1000 mL) was added, stirred for 30 min, and filtered via Büchner funnel. The off-white solid was triturated sequentially for 40 min in EtOAc (600 mL) and heptane (400 mL). The slurry was filtered via Büchner funnel and the solid was dried in an oven at 40° C., overnight to afford 6 as a light-yellow solid.

Scheme 1

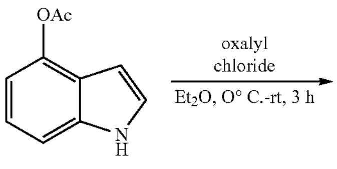

5

-continued

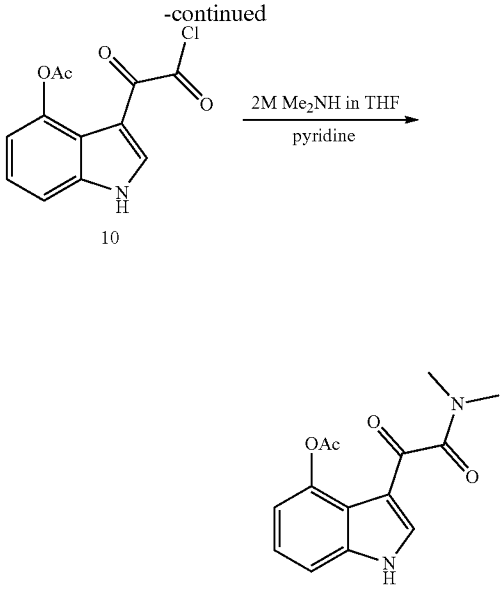

10

6

Scheme 2

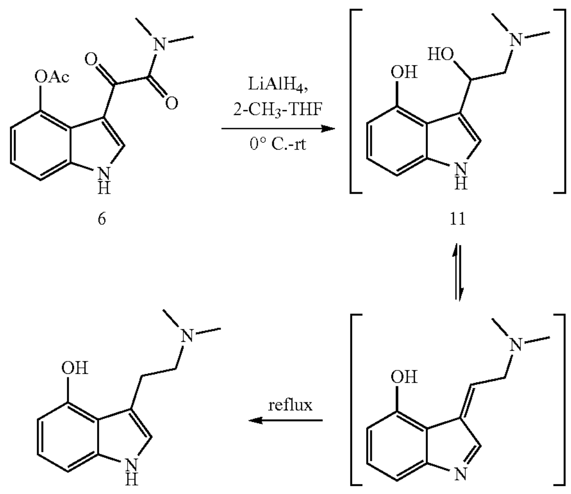

6

11

12

7

Synthesis of Compound 7 Psilocin

Procedure A: Synthesis of Compound 7 can be found in Scheme 2. A 2000 mL, four-necked, round-bottomed flask was equipped with an overhead stirrer, J-Kem temperature controller, a 250 mL dropping funnel, and rubber septum through which a positive pressure of dry $N_2$ was inserted. The septum was removed and the flask charged sequentially with 3-[2-(dimethylamino)-2-oxoacetyl]-1H-indol-4-yl acetate (6:31.5 g, 115 mmol) and 2-$CH_3$-THF (1000 mL). The flask was immersed in an ice-bath at 0° C., and a solution of 2.3 M $LiAlH_4$ in 2-$CH_3$-THF (140 mL, 322 mmol) was added through the 250 mL dropping funnel. The dropping funnel was rinsed with additional 2-$CH_3$-THF (20 mL). The $LiAlH_4$ solution was added dropwise at a rate to maintain a temperature below 20° C. After the addition, the ice-water bath was removed and the mixture stirred for 30 min. Analytical HPLC indicated a single major peak, which has been found to be the intermediate compound 11 (hydroxypsilocin intermediate). The light-yellow solution was heated to reflux (80° C.) with a heating mantle and became ivory-colored after 3 h. Accumulation of yellow solids was observed on the sides of the round-bottomed flask.

The reaction mixture was assayed by analytical HPLC, which showed completion of >90% to product peak 7. The heating mantle was removed, and the flask was allowed to cool to 50° C. The flask was again chilled to 20° C. The reaction was quenched by sequential addition of 3 drops of aq 1 M NaOH and 3 drops of deionized $H_2O$. The mixture was diluted with THF (500 mL) and stirred for 20 min. The mixture was filtered via Büchner funnel and the filtrate was kept under $N_2$. The filter cake was quickly reslurried with 200 mL of [10% solution of (7% ammonia in MeOH) in $CH_2Cl_2$] and THF (500 mL). The filtrates were then combined and concentrated to give a green solid. The solid] was triturated with 1:1 EtOAc/heptane (50 mL), then filtered via Büchner funnel. The dark green solid was dried in an oven at 40° C., overnight to provide dry psilocin (7) as a dark green solid.

Synthesis of Compound 11 Hydroxypsilocin

The synthesis of Compound 11 can be found in Scheme 2. Intermediate 11 was isolated by performing essentially the same reaction sequence described for compound 7 on a smaller scale except it was stirred at rt instead of reflux for 4 h. Following quench, the filtrate was concentrated, and the residue was purified by flash column chromatography ($SiO_2$, 100:10:1 $CH_2Cl_2$/$CH_3OH$/$NH_4OH$) to provide 11 as a gray solid.

Procedure B: The reduction step was carried out using essentially the same protocol described in Procedure A with 6 (40.21 g, 135.2 mmol) and 2.3 M $LiAlH_4$ in 2-$CH_3$-THF (188.1 mL, 432.5 mmol). The reaction was quenched by dropwise addition of THF/$H_2O$ (27:100, 50 mL) at a rate that kept the temperature below 30° C. Anhydrous $Na_2SO_4$ (100 g) was added followed by silica gel (50 g) and DCM (400 mL). The mixture was stirred for 10 min and was filtered via Büchner funnel. The filter cake was washed with DCM/$CH_3OH$ mixture (9:1, 1500 mL). The filtrates were then combined and concentrated to give a light green solid. The solid was triturated with 1:1 EtOAc/heptane (50 mL), then filtered via Büchner funnel. The off-white solid was dried in an oven at 40° C., overnight to provide dry psilocin (7) as an off-white solid.

Synthesis of Compound 9 Benzyl {3-[2-(Benzyldimethylammonio)ethyl]-1H-indol-4-yl} Phosphate The synthesis of Compound 9 can be found in Scheme 3. A 2000 mL, four-necked, round bottomed flask was equipped with an overhead stirrer, J-Kem temperature controller, a 100 mL dropping funnel, and rubber septum through which a positive pressure of dry $N_2$ inserted. The septum was removed and the flask was charged sequentially with psilocin (7:10.3 g, 60.2 mmol) and anhyd THF (500 mL). The mixture was stirred for 15 min and the flask was immersed in a solid CO2/acetone cooling bath at −78° C. When the internal temperature of the reaction reached −67° C., a solution of 2.5 M BuLi in hexanes (28.9 mL, 72.3 mmol) was added dropwise over a period of a few min and maintained the internal temperature reading below −60° C.

After stirring the olive-green colored reaction mixture for 10 min, tetrabenzyl pyrophosphate (35.7 g, 66.2 mmol) was added in one portion and the mixture was stirred well. After 1.5 h, the solid CO2/acetone cooing bath was removed and the temperature was allowed to slowly rise to −25° C., over 2 h, at which time LCMS showed completion of the reaction to compound 15 with no trace of compound 10 in the reaction mixture. Amino bound silica gel (30 g) was added in one portion and the reaction was diluted with EtOAc (600 mL). The dark mixture was filtered through a pad of Celite and washed with EtOAc (400 mL). The filter cake was reslurried for 10 min with EtOAc (400 mL) and again filtered. The combined filtrates were concentrated and transferred into a 500 mL single-necked roundbottomed flask. The gray oil was redissolved in DCM (100 mL) and heated with a heat gun to boiling for 5 min. The flask was allowed to reach rt and then held at 4° C., overnight. The crude grayish-colored zwitterion precipitate 9 was filtered via Büchner funnel, then triturated with DCM (4×100 mL). The zwitterion precipitate 9 was transferred into a 250 mL single-necked round-bottomed flask and thoroughly dried in the vacuum oven at 40° C., overnight to provide a light purple solid.

Scheme 3

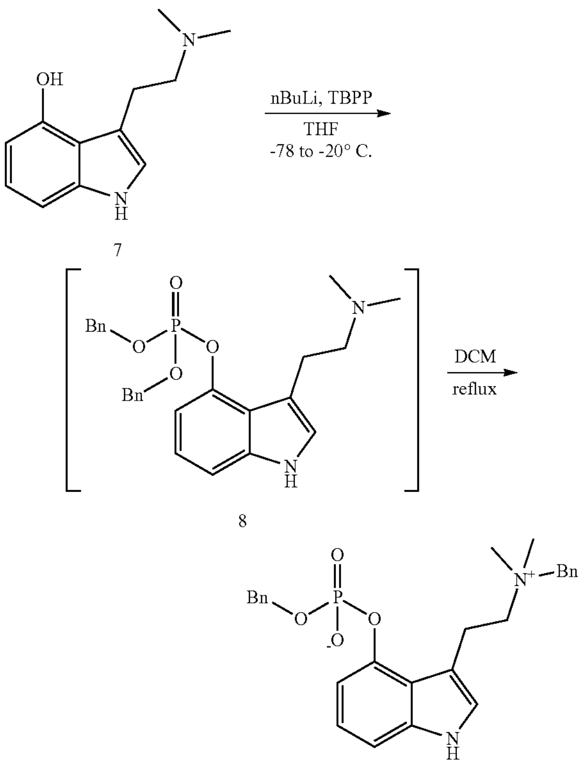

7

8

9

Synthesis of Amorphous (e.g., a-polymorphic) Psilocybin through Liquid-Liquid Extraction The synthesis of Compound 1, psilocybin, can be found in Scheme 4. Once synthesis of intermediate 9 was completed, the synthesis of amorphous (a-polymorphic) psilocybin 1, was achieved through the following steps. Into a 2000 mL round-bottomed flask was added 9 (16.9 g, 35.6 mmol) followed by $CH_3OH$ (1200 mL). The mixture was degassed and refilled with $N_2$, 10% Pd/C (1.1 g) was added and the mixture was degassed and refilled with a $H_2$ balloon at 1 atm. The reaction mixture was stirred overnight at rt. LCMS showed completion of the reaction with no starting material remaining (Subsequent reactions revealed that the hydrogenolysis was complete after 30 min). The flask was degassed, refilled with $N_2$ and the suspension was filtered through a pad of Celite via Büchner funnel. The filter pad was washed with $CH_3OH$ (500 mL). 150 mL of the reaction solution was diluted with 450 mL $H_2O$ and pH was adjusted to pH 9 with $NH_3$ (aq., 25%) and 2× extracted with 350 mL DCM at RT (RT=21.5 deg. C±2 deg. C). Aqueous phase was reduced in volume under reduced pressure (depletion of $CH_3OH$ and $NH_3$) to produce an aqueous solution of non-crystalline psilocybin 1.

Purity: >Purity was determined to be 98.3% as confirmed by Reverse Phase-HPLC at 267 nm (Agilent 1220 Infinity). Substitute Specification Clean Scheme 4

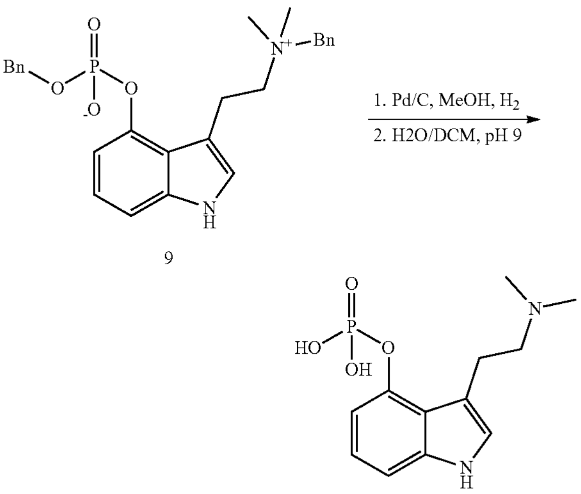

9

1

Example 3: Lyophilization and Spray Drying of Amorphous Psilocybin and Stability Studies Lyophilization (no sugars), XRPD, and NMR Analysis 50 mL of the aqueous solution from Example 2 (non-crystalline psilocybin 1) was lyophilized using a Christ Alpha 1-2 lyophilizer. The solution was transferred to round bottom flask (100 mL, NS29). The solution was filtered via 0.2 μm PTFE syringe filter and lyophilized at room temperature for 24 hours. The yield was 55 mg. The lyophilization yielded a fine colorless powder.

Polarizing Microscopy: Prior to XRPD analysis lyophilized powder was analyzed using polarizing light microscopy. Samples were confirmed to contain no crystalline structure prior to loading into borosilicate capillary for XRPD analysis. Equipment used was a Leitz (Wetzlar, Germany) Ortholux (model I) equipped with polarization condenser "Achr. 0.90 P" (Leitz Wetzlar Germany).

XRPD Methodology: Lyopholized powder was filled and sealed in a borosilicate capillary (diameter: 0.7 mm). Subsequently the powder diffraction pattern was recorded in transmissive Debeye-Scherrer geometry (device: STOE StadiP). A copper-source was used to produce Cu kα1-radiation (λ=1.540598 Å). An overview measurement was recorded in a range of 2-40° in 2θ, with a step width of 0.015° and a collection time of 5 s or 30 s per step. Detection of the diffracted X-ray beam was conducted using a single-photon counting strip detector (DECTRIS MYTHEN 1K) and qualitative evaluation of the diffractograms took place using the WinXPOW software (STOE).

FIG. 1 illustrates the XRPD of the psilocybin lyophilisate showing no sharp reflections which equate to an amorphous (e.g., a-polymorphic) phase as compared to a crystallized version of psilocybin as used as the reference spectrum.

Figure 2:
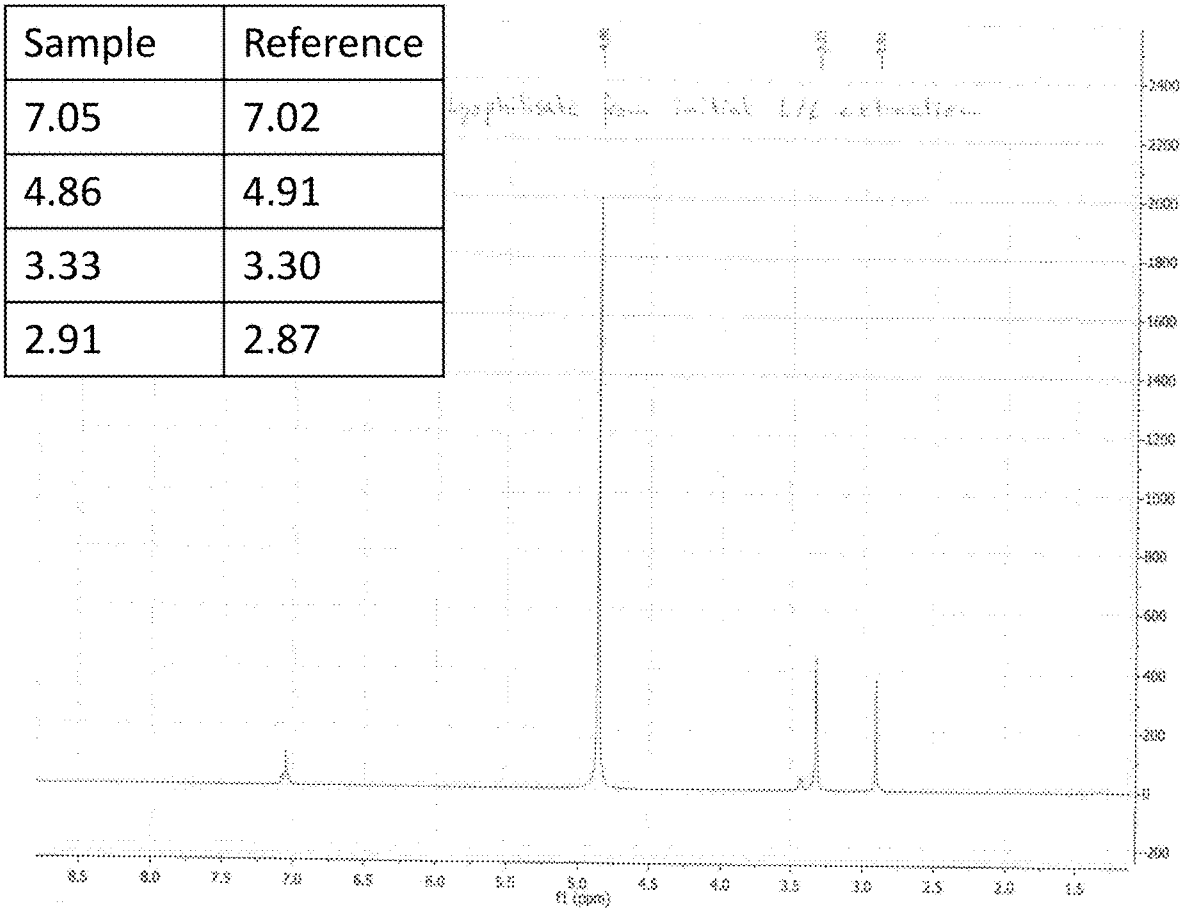
FIG. 2 illustrates a 1H NMR spectrum of lyophilized psilocybin. The inset table is a comparison between the lyophilized sample and the reference sample.

Proton NMR of the lyophilisate in methanol-D4 was conducted. The NMR was compared to a reference. The proton NMR confirmed the structure of the psilocybin lyophilisate (FIG. 2). Spray Drying of Psilocybin Seven psilocybin containing solutions were prepared and spray dried:

1. Psilocybin: Trehalose (50:50) 1% in $H_2O$→Sample ID HSR2305_01
2. Psilocybin: Trehalose (25:75) 1% in $H_2O$→Sample ID HSR2305_02
3. Psilocybin: Mannitol (25:75) 1% in $H_2O$→Sample ID HSR2305_03
4. Psilocybin: Trehalose (75:25) 1% in $H_2O$→Sample ID HSR2305_04
5. Psilocybin: Mannitol (75:25) 1% in $H_2O$→Sample ID HSR2305_05
6. Psilocybin: Mannitol (50:50) 1% in $H_2O$→Sample ID HSR2305_06
7. Psilocybin (100) 1% in $H_2O$→Sample ID HSR2305_07

The solutions were transferred to a round bottom flask for the experiments. Solutions 1-3 were completely dissolved, while solution 4-7 contained undissolved material and were therefore stirred continuously at room temperature during the experiment to ensure homogeneous product distribution using a compact stirrer IKA Ministars 20 Control with radial PTFE stirrer (Bola stirring shaft (Article No.: C382-02).

All solutions were dried with the nano spray dryer (Büchi, B-90). Regarding the product properties, it was found that an increased trehalose content led to improved flowability of the powder.

An increased mannitol content results in strong adhesion of the dried material to the deposition electrode, which can lead to lower yields for solutions containing mannitol.

For all experiments a stainless-steel spray membrane with a mesh size of 7 μm was used. Drying was carried out under nitrogen atmosphere (3% $O_2$) in closed circuit with a drying gas volume flow of 130 L/min.

The process parameters of the spray drying experiments can be found in Table 1.

In Table 1, the Tin[° C.] is temperature of the drying gas at the inlet to the drying chamber. Spray [%] corresponds to the frequency of piezoelectric membrane (is excited to vibrate by means of ultrasound 60 kHz). Pump Setting: 1—Pump rotation direction clockwise with normal speed, 2—pump rotation clockwise with double speed. $T_{cooling}$ is the temperature in the dehumidifier.

After analysis of sample HSR2305_03, the drying temperature was increased slightly, due to the strong adhesion of the product, incomplete drying was initially suspected. Since the product of HSR2305_05 again strongly adhered to the electrode, it is rather suspected that this product behavior may be due to the high mannitol content.

The product masses were measured with a scale with an accuracy of 50 mg. The product mass of HSR2305_05 was not determined.

The solution volume of HSR2305_07 was only 20 mL, therefore, in comparison to 40 mL of feed solution available for each of the other tests, less volume was sprayed in.

The test duration of the various experiments differed due to changes in the pump settings and slight clogging at the spray membrane presumed, which may have caused inhomogeneities of the spray stream. In general, all drying trials ran without problems.

Samples stored for 2-4 weeks at RT are analyzed by XRPD according to the following methodology: Spray-dried samples are filled and sealed in a borosilicate capillary (diameter: 0.7 mm). Subsequently the powder diffraction pattern is recorded in transmissive Debeye-Scherrer geometry (device: STOE StadiP). A copper-source is used to produce Cu kα1-radiation (λ=1.540598 Å). An overview measurement is recorded in a range of 2-40° in 2θ, with a step width of 0.015° and a collection time of 5 s per step. Detection of the diffracted X-ray beam is conducted using a single-photon counting strip detector (DECTRIS MYTHEN 1K) and qualitative evaluation of the diffractograms takes place using the WinXPOW software (STOE).

Lyophilization with Sugars

Seven psilocybin containing aqueous solutions (as previously prepared for spray drying experiment) were lyophilized with a Christ Alpha 1-2 lyophilizer:

1. Psilocybin: Trehalose (50:50) 1% in $H_2O$→Sample ID FSC2304_01_02
2. Psilocybin: Trehalose (25:75) 1% in $H_2O$→Sample ID FSC2304_01_03
3. Psilocybin: Mannitol (25:75) 1% in $H_2O$→Sample ID FSC2304_01_04
4. Psilocybin: Trehalose (75:25) 1% in $H_2O$→Sample ID FSC2304_01_05
5. Psilocybin: Mannitol (75:25) 1% in $H_2O$→Sample ID FSC2304_01_06

TABLE 1

| Sample ID | HSR2305_01 | HSR2305_02 | HSR2305_03 | HSR2305_04 | HSR2305_05 | HSR2305_06 | HSR2305_07 |
|---|---|---|---|---|---|---|---|
| $T_{in}$[° C.] | 110 | 110 | 110 | 120 | 120 | 120 | 120 |
| Spray [%] | 60 | 60 | 60 | 60 | 60 | 60 | 60 |
| Pumprate | 2 | 2 | 2 | 1 | 1 | 1 | 1 |
| $T_{cooling}$ [° C.] | 8 | 8 | 8 | 8 | 6 | 7 | 7 |
| Duration [min] | 31 | 49 | 35 | 50 | 49 | 52 | 42 |
| $M_{solution}$ [g] | 31.97 | 30.20 | 31.60 | 31.05 | 35.02 | 32.35 | 17.05 |
| $M_{product}$ [g] | 0.13 | 0.13 | 0.08 | 0.14 | — | 0.02 | 0.07 |

6. Psilocybin: Mannitol (50:50) 1% in $H_2O$→Sample ID FSC2304_01_07
7. Psilocybin (100) 1% in $H_2O$→Sample ID FSC2304_01_08

The solutions were transferred to round bottom flasks (100 mL, NS29) for the experiments. Solutions 4, 5 and 7 were gently heated to 40° C., to dissolve precipitated solids. All solutions were filtered via 0.2 μm PTFE syringe filter and lyophilized at room temperature for 24 hours. All samples were weighed after completion of lyophilization. Results can be found below. As expected, there was no significant loss of substance. The process parameters of the tests are listed in Table 2.

tative evaluation of the diffractograms took place using the WinXPOW software (STOE).

FIG. 3 illustrates no sharp reflexes in either of the psilocybin lyophilizate short scan sample (PSI LYO ST) or the psilocybin lyophilisate long scan sample (PSI LYO LT). Thus, following 1 week of storage at RT, the lack of sharp reflexes indicated (that in the absence of sugars or polymer) the psilocybin lyophilisate long and short scan samples surprisingly maintained a non-crystalline/amorphous phase. The results of the measurement indicates the absence of long-range ordering (i.e, crystallinity), of the psilocybin lyophilisate samples.

TABLE 2

| Sample ID | FSC2304_01_02 | FSC2304_01_03 | FSC2304_01_04 | FSC2304_01_05 | FSC2304_01_06 | FSC2304_01_07 | FSC2304_01_08 |
|---|---|---|---|---|---|---|---|
| $T_{st}$[° C.] | r.t. | r.t. | r.t. | r.t. | r.t. | r.t. | r.t. |
| $T_{cooling}$ [° C.] | −54 | −54 | −54 | −54 | −54 | −54 | −54 |
| P [mbar] | 0.01 | 0.01 | 0.01 | 0.01 | 0.01 | 0.01 | 0.01 |
| Duration [hr] | 24 | 24 | 24 | 24 | 24 | 24 | 24 |
| $M_{solution}$ [g] | 5.81 | 8.29 | 7.11 | 7.11 | 4.06 | 6.22 | 1.45 |
| $M_{product}$ [mg] | 57.9 | 83.1 | 70.8 | 71.0 | 40.7 | 61.9 | 14.4 |

In Table 2, Tst[° C.] is the temperature of the solution at the start of lyophilization, r.t, is room temperature of 21+/−2° C., $T_{cooling}$[° C.] is the temperature of the condenser, and P [mbar] is the pressure inside the lyophilizer.

Samples stored for 2-4 weeks at RT are analyzed by XRPD according to the following methodology: Lyophilized samples are filled and sealed in a borosilicate capillary (diameter: 0.7 mm). Subsequently the powder diffraction pattern is recorded in transmissive Debeye-Scherrer geometry (device: STOE StadiP). A copper-source is used to produce Cu kα1-radiation (λ=1.540598 Å). An overview measurement is recorded in a range of 2-40° in 2θ, with a step width of 0.015° and a collection time of 5 s per step. Detection of the diffracted X-ray beam is conducted using a single-photon counting strip detector (DECTRIS MYTHEN IK) and qualitative evaluation of the diffractograms takes place using the WinXPOW software (STOE).

Stability Studies

Samples from the lyophilization experiment (no sugar), were stored at room temperature (RT=25 deg. C) for 1 week. On day 1, samples were subjected to polarizing microscopy (as described above). Samples were confirmed to contain no crystalline structure. Samples tested following 1 week storage were identified as psilocybin lyophilisate long scan sample (PSI LYO LT) and psilocybin lyophilizate short scan sample (PSI LYO ST).

PSI LYO ST and PSI LYO LT were analyzed by XRPD according to the following methodology: Lyophilized powder was filled and sealed in a borosilicate capillary (diameter: 0.7 mm). Subsequently the powder diffraction pattern was recorded in transmissive Debeye-Scherrer geometry (device: STOE StadiP). A copper-source was used to produce Cu kα1-radiation (λ=1.540598 Å). An overview measurement was recorded in a range of 2-40° in 2θ, with a step width of 0.015° and a collection time of 30 s per step (PSI LYO LT) and 5 s per step (PSI LYO ST). Detection of the diffracted X-ray beam was conducted using a single-photon counting strip detector (DECTRIS MYTHEN 1K) and quali- Dissolution Assay A saturated solution of Psilocybin is generated in pure water (ReOS, degassed with $N_2$ (Exclusion of air (CO2), $N_2$ Quality 5.0). The conductivity of the solution is measured as a reference for a completely dissolved datapoint. The method is repeated with a new sample in a dried vessel, by adding substance, adding water, and inserting electrode with stirring. The conductivity of the solution will rise and the time at which 90% of the initial measurement is reached is (190). A Schott Instruments LAB 960 conductivity meter (range 500 mS/cm to 0.001 μS/cm) can be used (see http://en.gihonjumasentosa.com/product/schott-lab-960-conductivity-bench-laoratory-meter-p718127.aspx, the contents of which are incorporated herein by reference).

We claim:

1. A method of making a synthetic, amorphous psilocybin, the method comprising:

(a) providing a protected psilocybin;

(b) deprotecting the protected psilocybin in a reaction solvent to provide psilocybin;

(c) extracting the psilocybin from the reaction solvent into an aqueous medium and washing the aqueous medium with an organic solvent, wherein the psilocybin is purified by the extracting;

(d) concentrating the aqueous medium comprising the psilocybin; and (e) collecting the amorphous psilocybin, wherein the collected amorphous psilocybin is at least 95% pure without the need for crystallization.

2. The method of claim 1, additionally comprising a step of formulating a composition comprising the collected amorphous psilocybin.

3. The method of claim 2, wherein at least 50% of the composition is comprised of the amorphous psilocybin.

4. The method of claim 1, wherein the protected psilocybin is represented by the structure:

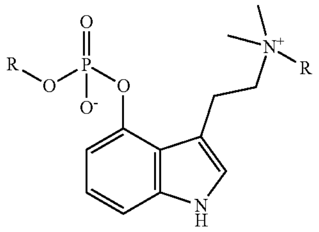

wherein: each R is independently hydrogen or a protecting group, provided at least one R is a protecting group.

5. The method of claim 4, wherein; the protecting group is benzyl and/or wherein deprotecting comprises hydrogenolysis.

6. The method of claim 1, wherein:

(a) the reaction solvent comprises an alcohol;

(b) the organic solvent comprises a halocarbon;

(c) the aqueous medium has a pH of about 9;

(d) the method does not require distillation of the aqueous medium; and/or (e) concentrating comprises spray drying or lyophilizing; and/or (f) the synthetic, amorphous psilocybin is at least 98% pure without the need for crystallization.

7. The method of claim 4, wherein all R groups are protecting groups.

8. The method of claim 4, wherein all R groups are hydrogen after deprotection.

9. The method of claim 1, wherein deprotecting comprises hydrogenolysis.

10. The method of claim 1, wherein the reaction solvent comprises an alcohol.

11. The method of claim 1, wherein the reaction solvent comprises methanol.

12. The method of claim 1, wherein the organic solvent comprises a halocarbon.

13. The method of claim 1, wherein the aqueous medium has a pH of about 9.

14. The method of claim 1, wherein concentrating comprises spray drying.

15. The method of claim 1, wherein concentrating comprises lyophilizing.

16. The method of claim 1, wherein the method does not require distillation of the aqueous medium.

17. The method of claim 1, wherein the synthetic, amorphous psilocybin is at least 98% pure without the need for crystallization.

18. The method of claim 1, wherein the extracting comprises a liquid-liquid extraction to purify the psilocybin.

* * * * *